US007186528B2

(12) United States Patent
Kirkpatrick et al.

(10) Patent No.: US 7,186,528 B2
(45) Date of Patent: Mar. 6, 2007

(54) METHOD FOR PREPARING A PHYSIOLOGICALLY ACTIVE IL-18 POLYPEPTIDE

(75) Inventors: Robert B. Kirkpatrick, King of Prussia, PA (US); Allan R. Shatzman, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 67 days.

(21) Appl. No.: 10/311,491

(22) PCT Filed: Jun. 11, 2001

(86) PCT No.: PCT/US01/18804

§ 371 (c)(1), (2), (4) Date: Dec. 16, 2002

(87) PCT Pub. No.: WO01/98455

PCT Pub. Date: Dec. 27, 2001

(65) Prior Publication Data

US 2003/0143198 A1 Jul. 31, 2003

Related U.S. Application Data

(60) Provisional application No. 60/211,832, filed on Jun. 15, 2000, provisional application No. 60/224,128, filed on Aug. 10, 2000, provisional application No. 60/264,923, filed on Jan. 30, 2001.

(51) Int. Cl.
*C12P 21/04* (2006.01)

(52) U.S. Cl. .................. 435/69.52; 435/325; 530/350; 530/351

(58) Field of Classification Search ............ 435/69.52, 435/69.1, 325
See application file for complete search history.

(56) References Cited

U.S. PATENT DOCUMENTS 5,914,254 A 6/1999 Mascarenhas et al. ..... 435/69.7
5,985,863 A 11/1999 Su et al. .................... 514/183
6,054,487 A 4/2000 Sekut et al. ............... 514/604

FOREIGN PATENT DOCUMENTS

EP 0821005 1/1998

OTHER PUBLICATIONS

Howard, Andrew D., et al.; "Human IL-1-beta Processing and Secretion in Recombinant Baculovirus-Infected Sf9 Cells is Blocked by the Cowpox Virus Serpin crmA", *Journal of Immunology*, vol. 154, No. 5, 1995, pp. 2321-2332.
Hsieh, C-L., et al., "Improved Gene Expression by a Modified Bicistronic Retroviral Vector", *Biochemical and Biophysical Research Communications*, vol. 214, No. 3, 1995, pp. 910-917.
Muneta, Yoshihiro, et al., "Efficient Production of Biologically Active Porcine Interleukin-18 by Coexpression with Porcine Caspase-1 Using a Baculovirus Expression System", *Journal of Interferon and Cytokine Research*, vol. 21, No. 2, pp. 125-130.
Hildinger, M, et al., "Bicistronic Retroviral Vectors for Combining Myeloprotection with Cell-surface Marking", *Gene Therapy*, vol. 6, No. 7, 1999, pp. 1222-1230.
Fassay. et al., "Enzymatic Activity of Two Caspases Related to Interleukin-1beta-Converting Enzyme", *Eur. J. Biochem.*, 253(1): 76-83 (1998).
Garcia-Calvo, et al., "Purification and Catalytic Properties of Human Caspase Family Members", *Cell Death and Diff.*, 6(4): 362-369 (1999).
Ghayur, et al., "Caspase-1 Processes IFN-Gamma-Inducing Factor and Regulates LPS-Induced IFN-Gamma Production". *Nature*. 389: 619-623 (1997).
Munday, et al., "Molecular Cloning and Pro-Apoptotic Activity of ICErelII and ICEeIII. Members of the ICE/CED-3 Family of Cysteine Proteases", *J. Biol. Chem.*, 270: 15870-15876 (1995).
Ushio, et al., "Cloning of the cDNA for Human IFN-Gamma-Inducing Factor, Expression in *Eschericha coli.* and Studies on the Biologic Activities of the Protein". *J. Immunol.*, 156:4274-4279 (1996).

*Primary Examiner*—Lorraine Spector
*Assistant Examiner*—Dong Jiang
(74) *Attorney, Agent, or Firm*—Elizabeth J. Hecht; Edward R. Gimmi; Charles M. Kinzig

(57) ABSTRACT

A method for producing a physiologically active polypeptide, comprising contacting a precursor polypeptide with an activating enzyme, or co-expressing the polypeptide with an activating protease.

1 Claim, 42 Drawing Sheets

FIGURE 1

SEQ ID NO:1

1 MAAEPVEDNC INFVAMKFID NTLYFIAEDD ENLESDYFGK LESKLSVIRN
51 LNDQVLFIDQ GNRPLFEDMT DSDCRDNAPR TIFIISMYKD SQPRGMAVTI
101 SVKCEKISTL SCENKIISFK EMNPPDNIKD TKSDIIFFQR SVPGHDNKMQ
151 FESSSYEGYF LACEKERDLF KLILKKEDEL GDRSIMFTVQ NED

FIGURE 2

SEQ ID NO:2

1 50
ATGGCTGCTG AACCAGTAGA AGACAATTGC ATCAACTTTG TGGCAATGAA
51 100
ATTTATTGAC AATACGCTTT ACTTTATAGC TGAAGATGAT GAAAACCTGG
101 150
AATCAGATTA CTTTGGCAAG CTTGAGAGCA AACTATCGGT CATtCGTAAT
151 200
TTAAATGACC AGGTCCTATT TATCGACCAA GGGAATCGTC CACTATTCGA
201 250
GGACATGACA GACAGTGACT GCCGAGACAA TGCGCCGCGA ACCATtTTCA
251 300
TTATATCTAT GTACAAGGAT TCTCAGCCGC GCGGAATGGC CGTAACTATT
301 350
TCTGTCAAAT GTGAAAAGAT ATCCACGCTG TCGTGTGAGA ACAAgATtAT
351 400
tAGTTTCAAA GAGATGAATC CGCCGGATAA TATCAAGGAC ACGAAGTCTG
401 450
ATATCATATT TTTCCAGCGC AGCGTGCCGG GGCACGATAA CAAGATGCAA
451 500
TTTGAATCAT CCAGCTATGA AGGGTACTTT CTTGCATGCG AGAAGGAACG
501 550
CGATCTCTTT AAACTTATTT TAAAGAAAGA GGACGAGCTA GGCGATCGCA
551 582
GCATtATGTT CACTGTCCAA AATGAAGACT AG

FIGURE 3

SEQ ID NO:3

1 YFGKLESKLS VIRNLNDQVL FIDQGNRPLF EDMTDSDCRD NAPRTIFIIS

51 MYKDSQPRGM AVTISVKCEK ISTLSCENKI ISFKEMNPPD NIKDTKSDII

101 FFQRSVPGHD NKMQFESSSY EGYFLACEKE RDLFKLILKK EDELGDRSIM

151 FTVQNED

FIGURE 4

SEQ ID NO:4

1 MGHHHHHHGA LKLCPHEEFL RLCKERAEEI YPIKERNNRT RLALIICNTE
51 FDHLPPRNGA DFDITGMKEL LEGLDYSVDV EENLTARDME SALRAFATRP
101 EHKSSDSTFL VLMSHGILEG ICGTVHDEKK PDVLLYDTIF QIFNNRNCLS
151 LKDKPKVIIV QACRGANRGE LWVRDSPTSL EVASSQSSEN LEEDAVYKTH
201 VEKDFIAFCS STPHNVSWRD STMGSIFITQ LITCFQKYSW CCHLEEVFRK
252 VQQSFETPRA KAQMPTIERL SMTRYFYLFP GN

FIGURE 5

SEQ ID NO: 5

```
1                                                 50
ATGGGCCATC ATCATCATCA TCATGGCGCC CTCAAGCTTT GTCCTCATGA
51                                               100
AGAATTCCTG AGACTATGTA AAGAAAGAGC TGAAGAGATC TATCCAATAA
101                                              150
AGGAGAGAAA CAACCGCACA CGCCTGGCTC TCATCATATG CAATACAGAG
151                                              200
TTTGACCATC TGCCTCCGAG GAATGGAGCT GACTTTGACA TCACAGGGAT
201                                              250
GAAGGAGCTA CTTGAGGGTC TGGACTATAG TGTAGATGTA GAAGAGAATC
251                                              300
TGACAGCCAG GGATATGGAG TCAGCGCTGA GGGCATTTGC TACCAGACCA
301                                              350
GAGCACAAGT CCTCTGACAG CACATTCTTG GTACTCATGT CTCATGGCAT
351                                              400
CCTGGAGGGA ATCTGCGGAA CTGTGCATGA TGAGAAAAAA CCAGATGTGC
401                                              450
TGCTTTATGA CACCATCTTC CAGATATTCA ACAACCGCAA CTGCCTCAGT
451                                              500
CTGAAGGACA AACCCAAGGT CATCATTGTC CAGGCCTGCA GAGGTGCAAA
501                                              550
CCGTGGGGAA CTGTGGGTCA GAGACTCTCC AGCATCCTTG GAAGTGGCCT
551                                              600
CTTCACAGTC ATCTGAGAAC CTGGAGGAAG ATGCTGTTTA CAAGACCCAC
601                                              650
GTGGAGAAGG ACTTCATTGC TTTCTGCTCT TCAACGCCAC ACAACGTGTC
651                                              700
CTGGAGAGAC AGCACAATGG GCTCTATCTT CATCACACAA CTCATCACAT
701                                              750
GCTTCCAGAA ATATTCTTGG TGCTGCCACC TAGAGGAAGT ATTTCGGAAG
751                                              800
GTACAGCAAT CATTTGAAAC TCCAAGGGCC AAAGCTCAAA TGCCCACCAT
801                                             849
AGAACGACTG TCCATGACAA GATATTTCTA CCTCTTTCCT GGCAATTGA
```

FIGURE 6

SEQ ID NO:6

```
1    MGHHHHHHGI LKLCPREEFL RLCKKNHDEI YPIKKREDRR RLALIICNTK
51   FDHLPARNGA HYDIVGMKRL LQGLGYTVVD EKNLTARDME SVLRAFAARP
101  EHKSSDSTFL VLMSHGILEG ICGTAHKKKK PDVLLYDTIF QIFNNRNCLS
151  LKDKPKVIIV QACRGEKHGE LWVRDSPASL AVISSQSSEN LEADSVCKIH
201  EEKDFIAFCS STPHNVSWRD RTRGSIFITE LITCFQKYSC CCHLMEIFRK
251  VQKSFEVPQA KAQMPTIERA TLTRDFYLFP GN
```

FIGURE 7

SEQ ID NO:7

```
1                                                    50
ATGGGCCATC ATCATCATCA TCATGGCATA CTCAAACTTT GTCCTCGTGA
51                                                  100
AGAATTCCTG AGACTGTGTA AAAAAAATCA TGATGAGATC TATCCAATAA
101                                                 150
AAAAGAGAGA GGACCGCAGA CGCCTGGCTC TCATCATATG CAATACAAAG
151                                                 200
TTTGATCACC TGCCTGCAAG GAATGGGGCT CACTATGACA TCGTGGGGAT
201                                                 250
GAAAAGGCTG CTTCAAGGCC TGGGCTACAC TGTGGTTGAC GAAAAGAATC
251                                                 300
TCACAGCCAG GGATATGGAG TCAGTGCTGA GGGCATTTGC TGCCAGACCA
301                                                 350
GAGCACAAGT CCTCTGACAG CACGTTCTTG GTACTCATGT CTCATGGCAT
351                                                 400
CCTAGAGGGA ATCTGCGGAA CTGCGCATAA AAAGAAAAAA CCGGATGTGC
401                                                 450
TGCTTTATGA CACCATCTTC CAGATATTCA ACAACCGCAA CTGCCTCAGT
451                                                 500
CTAAAGGACA AACCCAAGGT CATCATTGTC CAGGCCTGCA GAGGTGAAAA
501                                                 550
ACATGGGGAA CTCTGGGTCA GAGACTCTCC AGCATCCTTG GCAGTCATCT
551                                                 600
CTTCACAGTC ATCTGAGAAC CTGGAGGCAG ATTCTGTTTG CAAGATCCAC
601                                                 650
GAGGAGAAGG ACTTCATTGC TTTCTGTTCT TCAACACCAC ATAACGTGTC
651                                                 700
CTGGAGAGAC CGCACAAGGG GCTCCATCTT CATTACGGAA CTCATCACAT
701                                                 750
GCTTCCAGAA ATATTCTTGC TGCTGCCACC TAATGGAAAT ATTTCGGAAG
751                                                 800
GTACAGAAAT CATTTGAAGT TCCACAGGCT AAAGCCCAGA TGCCCACCAT
801                                               849
AGAACGAGCA ACCTTGACAA GAGATTTCTA CCTCTTTCCT GGCAATTGA
```

FIGURE 9

SEQ ID NO:8

```
1                                                  50
AGATCTCGAT CCCGCGAAAT TAATACGACT CACTATAGGG GAATTGTGAG
51                                                100
CGGATAACAA TTCCCCTCTA GACCACACCT taaggaggat ataacatATG
101                                               150
GCTGCTGAAC CAGTAGAAGA CAATTGCATC AACTTTGTGG CAATGAAATT
151                                               200
TATTGACAAT ACGCTTTACT TTATAGCTGA AGATGATGAA AACCTGGAAT
201                                               250
CAGATTACTT TGGCAAGCTT GAGAGCAAAC TATCGGTCAT tCGTAATTTA
251                                               300
AATGACCAGG TCCTATTTAT CGACCAAGGG AATCGTCCAC TATTCGAGGA
301                                               350
CATGACAGAC AGTGACTGCC GAGACAATGC GCCGCGAACC ATtTTCATTA
351                                               400
TATCTATGTA CAAGGATTCT CAGCCGCGCG GAATGGCCGT AACTATTTCT
401                                               450
GTCAAATGTG AAAAGATATC CACGCTGTCG TGTGAGAACA AgATtATtAG
451                                               500
TTTCAAAGAG ATGAATCCGC CGGATAATAT CAAGGACACG AAGTCTGATA
501                                               550
TCATATTTTT CCAGCGCAGC GTGCCGGGGC ACGATAACAA GATGCAATTT
551                                               600
GAATCATCCA GCTATGAAGG GTACTTTCTT GCATGCGAGA AGGAACGCGA
601                                               650
TCTCTTTAAA CTTATTTTAA AGAAAGAGGA CGAGCTAGGC GATCGCAGCA
651                                               700
TtATGTTCAC TGTCCAAAAT GAAGACTAGT ggaggatata aTACCAgGaa
701                                               750
taaataaaat ccatgGgcca tcatcatcat catcatggcG CCCTCAAGCT
751                                               800
TTGTCCTCAT GAAGAATTCC TGAGACTATG TAAAGAAAGA GCTGAAGAGA
801                                               850
TCTATCCAAT AAAGGAGAGA AACAACCGCA CACGCCTGGC TCTCATCATA
851                                               900
TGCAATACAG AGTTTGACCA TCTGCCTCCG AGGAATGGAG CTGACTTTGA
```

FIGURE 9 (continued)

```
901                                                950
CATCACAGGG ATGAAGGAGC TACTTGAGGG TCTGGACTAT AGTGTAGATG
951                                               1000
TAGAAGAGAA TCTGACAGCC AGGGATATGG AGTCAGCGCT GAGGGCATTT
1001                                              1050
GCTACCAGAC CAGAGCACAA GTCCTCTGAC AGCACATTCT TGGTACTCAT
1051                                              1100
GTCTCATGGC ATCCTGGAGG GAATCTGCGG AACTGTGCAT GATGAGAAAA
1101                                              1150
AACCAGATGT GCTGCTTTAT GACACCATCT TCCAGATATT CAACAACCGC
1151                                              1200
AACTGCCTCA GTCTGAAGGA CAAACCCAAG GTCATCATTG TCCAGGCCTG
1201                                              1250
CAGAGGTGCA AACCGTGGGG AACTGTGGGT CAGAGACTCT CCAGCATCCT
1251                                              1300
TGGAAGTGGC CTCTTCACAG TCATCTGAGA ACCTGGAGGA AGATGCTGTT
1301                                              1350
TACAAGACCC ACGTGGAGAA GGACTTCATT GCTTTCTGCT CTTCAACGCC
1351                                              1400
ACACAACGTG TCCTGGAGAG ACAGCACAAT GGGCTCTATC TTCATCACAC
1401                                              1450
AACTCATCAC ATGCTTCCAG AAATATTCTT GGTGCTGCCA CCTAGAGGAA
1451                                              1500
GTATTTCGGA AGGTACAGCA ATCATTTGAA ACTCCAAGGG CCAAAGCTCA
1501                                              1550
AATGCCCACC ATAGAACGAC TGTCCATGAC AAGATATTTC TACCTCTTTC
1551                                              1600
CTGGCAATTG AAAATGGATC CGAATTCGAG CTCCGTCGAC AAGCTTGCGG
1601                                              1650
CCGCACTCGA GCACCACCAC CACCACCACT GAGATCCGGC TGCTAACAAA
1651                                              1700
GCCCGAAAGG AAGCTGAGTT GGCTGCTGCC ACCGCTGAGC AATAACTAGC
1701                                   1743
ATAACCCCTT GGGGCCTCTA AACGGGTCTT GAGGGGTTTT TTG
```

FIGURE 10

```
                            T7 promoter
     AGATCTCGATCCCGCGAAATTAATACGACTCACTATAGGGGAATTGTGAGCGGATAACAA
4964 ------+---------+---------+---------+---------+---------+--- 5023
     TCTAGAGCTAGGGCGCTTTAATTATGCTGAGTGATATCCCCTTAACACTCGCCTATTGTT

                          Shine-Dalgarno      ProIL18 start
     TTCCCCTCTAGACCACACCTtaaggaggatataacatATGGCTGCTGAACCAGTAGAAGA
5024 ------+---------+---------+---------+---------+---------+--- 5083
     AAGGGGAGATCTGGTGTGGAattcctcctatattgtaTACCGACGACTTGGTCATCTTCT

b                                              M  A  A  E  P  V  E  D  -

     CAATTGCATCAACTTTGTGGCAATGAAATTTATTGACAATACGCTTTACTTTATAGCTGA
5084 ------+---------+---------+---------+---------+---------+--- 5143
     GTTAACGTAGTTGAAACACCGTTACTTTAAATAACTGTTATGCGAAATGAAATATCGACT

b      N  C  I  N  F  V  A  M  K  F  I  D  N  T  L  Y  F  I  A  E  -
                                Start of mature IL18
     AGATGATGAAAACCTGGAATCAGATTACTTTGGCAAGCTTGAGAGCAAACTATCGGTCAT
5144 ------+---------+---------+---------+---------+---------+--- 5203
     TCTACTACTTTTGGACCTTAGTCTAATGAAACCGTTCGAACTCTCGTTTGATAGCCAGTA

b      D  D  E  N  L  E  S  D  Y  F  G  K  L  E  S  K  L  S  V  I  -

     tCGTAATTTAAATGACCAGGTCCTATTTATCGACCAAGGGAATCGTCCACTATTCGAGGA
5204 ------+---------+---------+---------+---------+---------+--- 5263
     aGCATTAAATTTACTGGTCCAGGATAAATAGCTGGTTCCCTTAGCAGGTGATAAGCTCCT

b      R  N  L  N  D  Q  V  L  F  I  D  Q  G  N  R  P  L  F  E  D  -

     CATGACAGACAGTGACTGCCGAGACAATGCGCCGCGAACCATtTTCATTATATCTATGTA
5264 ------+---------+---------+---------+---------+---------+--- 5323
     GTACTGTCTGTCACTGACGGCTCTGTTACGCGGCGCTTGGTAaAAGTAATATAGATACAT

b      M  T  D  S  D  C  R  D  N  A  P  R  T  I  F  I  I  S  M  Y  -
```

FIGURE 10 (continued)

```
        CAAGGATTCTCAGCCGCGCGGAATGGCCGTAACTATTTCTGTCAAATGTGAAAAGATATC
   5324 ------+---------+---------+---------+---------+---------+--- 5383
        GTTCCTAAGAGTCGGCGCGCCTTACCGGCATTGATAAAGACAGTTTACACTTTTCTATAG

b        K  D  S  Q  P  R  G  M  A  V  T  I  S  V  K  C  E  K  I  S  -

        CACGCTGTCGTGTGAGAACAAgATtATtAGTTTCAAAGAGATGAATCCGCCGGATAATAT
   5384 ------+---------+---------+---------+---------+---------+--- 5443
        GTGCGACAGCACACTCTTGTTcTAaTAaTCAAAGTTTCTCTACTTAGGCGGCCTATTATA

b        T  L  S  C  E  N  K  I  I  S  F  K  E  M  N  P  P  D  N  I  -

        CAAGGACACGAAGTCTGATATCATATTTTTCCAGCGCAGCGTGCCGGGGCACGATAACAA
   5444 ------+---------+---------+---------+---------+---------+--- 5503
        GTTCCTGTGCTTCAGACTATAGTATAAAAAGGTCGCGTCGCACGGCCCCGTGCTATTGTT

b        K  D  T  K  S  D  I  I  F  F  Q  R  S  V  P  G  H  D  N  K  -

        GATGCAATTTGAATCATCCAGCTATGAAGGGTACTTTCTTGCATGCGAGAAGGAACGCGA
   5504 ------+---------+---------+---------+---------+---------+--- 5563
        CTACGTTAAACTTAGTAGGTCGATACTTCCCATGAAAGAACGTACGCTCTTCCTTGCGCT

b        M  Q  F  E  S  S  S  Y  E  G  Y  F  L  A  C  E  K  E  R  D  -

        TCTCTTTAAACTTATTTTAAAGAAAGAGGACGAGCTAGGCGATCGCAGCATtATGTTCAC
   5564 ------+---------+---------+---------+---------+---------+--- 5623
        AGAGAAATTTGAATAAAATTTCTTTCTCCTGCTCGATCCGCTAGCGTCGTAaTACAAGTG

b        L  F  K  L  I  L  K  K  E  D  E  L  G  D  R  S  I  M  F  T  -

                           Defective Shine-Dalgarno    Start of Caspase-4
        TGTCCAAAATGAAGACTAGTggaggatataaTACCAgGaataaataaaatccatgGgcca
   5624 ------+---------+---------+---------+---------+---------+--- 5683
        ACAGGTTTTACTTCTGATCAcctcctatattATGGTcCttatttattttaggtacCcggt

b        V  Q  N  E  D                                M  G  H  -
```

FIGURE 10 (continued)

```
         tcatcatcatcatcatggcGCCCTCAAGCTTTGTCCTCATGAAGAATTCCTGAGACTATG
    5684 ------+---------+---------+---------+---------+---------+--- 5743
         agtagtagtagtagtaccgCGGGAGTTCGAAACAGGAGTACTTCTTAAGGACTCTGATAC

b         H  H  H  H  H  G  A  L  K  L  C  P  H  E  E  F  L  R  L  C  -

         TAAAGAAAGAGCTGAAGAGATCTATCCAATAAAGGAGAGAAACAACCGCACACGCCTGGC
    5744 ------+---------+---------+---------+---------+---------+--- 5803
         ATTTCTTTCTCGACTTCTCTAGATAGGTTATTTCCTCTCTTTGTTGGCGTGTGCGGACCG

b         K  E  R  A  E  E  I  Y  P  I  K  E  R  N  N  R  T  R  L  A  -

         TCTCATCATATGCAATACAGAGTTTGACCATCTGCCTCCGAGGAATGGAGCTGACTTTGA
    5804 ------+---------+---------+---------+---------+---------+--- 5863
         AGAGTAGTATACGTTATGTCTCAAACTGGTAGACGGAGGCTCCTTACCTCGACTGAAACT

b         L  I  I  C  N  T  E  F  D  H  L  P  P  R  N  G  A  D  F  D  -

         CATCACAGGGATGAAGGAGCTACTTGAGGGTCTGGACTATAGTGTAGATGTAGAAGAGAA
    5864 ------+---------+---------+---------+---------+---------+--- 5923
         GTAGTGTCCCTACTTCCTCGATGAACTCCCAGACCTGATATCACATCTACATCTTCTCTT

b         I  T  G  M  K  E  L  L  E  G  L  D  Y  S  V  D  V  E  E  N  -

         TCTGACAGCCAGGGATATGGAGTCAGCGCTGAGGGCATTTGCTACCAGACCAGAGCACAA
    5924 ------+---------+---------+---------+---------+---------+--- 5983
         AGACTGTCGGTCCCTATACCTCAGTCGCGACTCCCGTAAACGATGGTCTGGTCTCGTGTT

b         L  T  A  R  D  M  E  S  A  L  R  A  F  A  T  R  P  E  H  K  -

         GTCCTCTGACAGCACATTCTTGGTACTCATGTCTCATGGCATCCTGGAGGGAATCTGCGG
    5984 ------+---------+---------+---------+---------+---------+--- 6043
         CAGGAGACTGTCGTGTAAGAACCATGAGTACAGAGTACCGTAGGACCTCCCTTAGACGCC

b         S  S  D  S  T  F  L  V  L  M  S  H  G  I  L  E  G  I  C  G  -

         AACTGTGCATGATGAGAAAAAACCAGATGTGCTGCTTTATGACACCATCTTCCAGATATT
    6044 ------+---------+---------+---------+---------+---------+--- 6103
         TTGACACGTACTACTCTTTTTTGGTCTACACGACGAAATACTGTGGTAGAAGGTCTATAA
```

FIGURE 10 (continued)

```
b         T  V  H  D  E  K  K  P  D  V  L  L  Y  D  T  I  F  Q  I  F  -
         CAACAACCGCAACTGCCTCAGTCTGAAGGACAAACCCAAGGTCATCATTGTCCAGGCCTG
    6104 ------+---------+---------+---------+---------+---------+--- 6163
         GTTGTTGGCGTTGACGGAGTCAGACTTCCTGTTTGGGTTCCAGTAGTAACAGGTCCGGAC

b         N  N  R  N  C  L  S  L  K  D  K  P  K  V  I  I  V  Q  A  C  -

         CAGAGGTGCAAACCGTGGGGAACTGTGGGTCAGAGACTCTCCAGCATCCTTGGAAGTGGC
    6164 ------+---------+---------+---------+---------+---------+--- 6223
         GTCTCCACGTTTGGCACCCCTTGACACCCAGTCTCTGAGAGGTCGTAGGAACCTTCACCG

b         R  G  A  N  R  G  E  L  W  V  R  D  S  P  A  S  L  E  V  A  -

         CTCTTCACAGTCATCTGAGAACCTGGAGGAAGATGCTGTTTACAAGACCCACGTGGAGAA
    6224 ------+---------+---------+---------+---------+---------+--- 6283
         GAGAAGTGTCAGTAGACTCTTGGACCTCCTTCTACGACAAATGTTCTGGGTGCACCTCTT

b         S  S  Q  S  S  E  N  L  E  E  D  A  V  Y  K  T  H  V  E  K  -

         GGACTTCATTGCTTTCTGCTCTTCAACGCCACACAACGTGTCCTGGAGAGACAGCACAAT
    6284 ------+---------+---------+---------+---------+---------+--- 6343
         CCTGAAGTAACGAAAGACGAGAAGTTGCGGTGTGTTGCACAGGACCTCTCTGTCGTGTTA

b         D  F  I  A  F  C  S  S  T  P  H  N  V  S  W  R  D  S  T  M  -

         GGGCTCTATCTTCATCACACAACTCATCACATGCTTCCAGAAATATTCTTGGTGCTGCCA
    6344 ------+---------+---------+---------+---------+---------+--- 6403
         CCCGAGATAGAAGTAGTGTGTTGAGTAGTGTACGAAGGTCTTTATAAGAACCACGACGGT

b         G  S  I  F  I  T  Q  L  I  T  C  F  Q  K  Y  S  W  C  C  H  -

         CCTAGAGGAAGTATTTCGGAAGGTACAGCAATCATTTGAAACTCCAAGGGCCAAAGCTCA
    6404 ------+---------+---------+---------+---------+---------+--- 6463
         GGATCTCCTTCATAAAGCCTTCCATGTCGTTAGTAAACTTTGAGGTTCCCGGTTTCGAGT

b         L  E  E  V  F  R  K  V  Q  Q  S  F  E  T  P  R  A  K  A  Q  -

         AATGCCCACCATAGAACGACTGTCCATGACAAGATATTTCTACCTCTTTCCTGGCAATTG
    6464 ------+---------+---------+---------+---------+---------+--- 6523
         TTACGGGTGGTATCTTGCTGACAGGTACTGTTCTATAAAGATGGAGAAAGGACCGTTAAC
```

```
b        M  P  T  I  E  R  L  S  M  T  R  Y  F  Y  L  F  P  G  N  *  -

         AAAATGGATCCGAATTCGAGCTCCGTCGACAAGCTTGCGGCCGCACTCGAGCACCACCAC
    6524 ------+---------+---------+---------+---------+---------+--- 6583
         TTTTACCTAGGCTTAAGCTCGAGGCAGCTGTTCGAACGCCGGCGTGAGCTCGTGGTGGTG

b        K  W  I  R  I  R  A  P  S  T  S  L  R  P  H  S  S  T  T  T  -

         CACCACCACTGAGATCCGGCTGCTAACAAAGCCCGAAAGGAAGCTGAGTTGGCTGCTGCC
    6584 ------+---------+---------+---------+---------+---------+--- 6643
         GTGGTGGTGACTCTAGGCCGACGATTGTTTCGGGCTTTCCTTCGACTCAACCGACGACGG

b        T  T  T  E  I  R  L  L  T  K  P  E  R  K  L  S  W  L  L  P  -
                                   T7 Terminator
         ACCGCTGAGCAATAACTAGCATAACCCCTTGGGGCCTCTAAACGGGTCTTGAGGGGTTTT
    6644 ------+---------+---------+---------+---------+---------+--- 6703
         TGGCGACTCGTTATTGATCGTATTGGGGAACCCCGGAGATTTGCCCAGAACTCCCCAAAA

b        P  L  S  N  N  *  H  N  P  L  G  P  L  N  G  S  *  G  V  F  -

         TTG
    6704 --- 6706
         AAC
```

FIGURE 13

SEQ ID NO:9

1 50
ATGGCTGCTG AACCAGTAGA AGACAATTGC ATCAACTTTG TGGCAATGAA
51 100
ATTTATTGAC AATACGCTTT ACTTTATAGC TGAAGATGAT GAAAACCTGG
101 150
AATCAGATTA CTTTGGCAAG CTTGAGAGCA AACTATCGGT CATTCGTAAT
151 200
TTAAATGACC AGGTCCTATT TATCGACCAA GGGAATCGTC CACTATTCGA
201 250
GGACATGACA GACAGTGACT GCCGAGACAA TGCGCCGCGA ACCATTTTCA
251 300
TTATATCTAT GTACAAGGAT TCTCAGCCGC GCGGAATGGC CGTAACTATT
301 350
TCTGTCAAAT GTGAAAAGAT ATCCACGCTG TCGTGTGAGA ACAAGATTAT
351 400
TAGTTTCAAA GAGATGAATC CGCCGGATAA TATCAAGGAC ACGAAGTCTG
401 450
ATATCATATT TTTCCAGCGC AGCGTGCCGG GGCACGATAA CAAGATGCAA
451 500
TTTGAATCAT CCAGCTATGA AGGGTACTTT CTTGCATGCG AGAAGGAACG
501 550
CGATCTCTTT AAACTTATTT TAAAGAAAGA GGACGAGCTA GGCGATCGCA
551 600
IGCATTATGTT CACTGTCCAA AATGAAGACT AGTGGAGGAT ATAATACCAG
601 650
GAATAAATAA AATCCATGGG CCATCATCAT CATCATCATG GCATACTCAA
651 700
ACTTTGTCCT CGTGAAGAAT TCCTGAGACT GTGTAAAAAA AATCATGATG
701 750
AGATCTATCC AATAAAAAAG AGAGAGGACC GCAGACGCCT GGCTCTCATC
751 800
ATATGCAATA CAAAGTTTGA TCACCTGCCT GCAAGGAATG GGGCTCACTA
801 850
TGACATCGTG GGGATGAAAA GGCTGCTTCA AGGCCTGGGC TACACTGTGG
851 900
TTGACGAAAA GAATCTCACA GCCAGGGATA TGGAGTCAGT GCTGAGGGCA
901 950
TTTGCTGCCA GACCAGAGCA CAAGTCCTCT GACAGCACGT TCTTGGTACT

FIGURE 13 (continued)

```
951                                                1000
CATGTCTCAT GGCATCCTAG AGGGAATCTG CGGAACTGCG CATAAAAAGA
1001                                               1050
AAAAACCGGA TGTGCTGCTT TATGACACCA TCTTCCAGAT ATTCAACAAC
1051                                               1100
CGCAACTGCC TCAGTCTAAA GGACAAACCC AAGGTCATCA TTGTCCAGGC
1101                                               1150
CTGCAGAGGT GAAAAACATG GGGAACTCTG GGTCAGAGAC TCTCCAGCAT
1151                                               1200
CCTTGGCAGT CATCTCTTCA CAGTCATCTG AGAACCTGGA GGCAGATTCT
1201                                               1250
GTTTGCAAGA TCCACGAGGA GAAGGACTTC ATTGCTTTCT GTTCTTCAAC
1251                                               1300
ACCACATAAC GTGTCCTGGA GAGACCGCAC AAGGGGCTCC ATCTTCATTA
1301                                               1350
CGGAACTCAT CACATGCTTC CAGAAATATT CTTGCTGCTG CCACCTAATG
1351                                               1400
GAAATATTTC GGAAGGTACA GAAATCATTT GAAGTTCCAC AGGCTAAAGC
1401                                               1450
CCAGATGCCC ACCATAGAAC GAGCAACCTT GACAAGAGAT TTCTACCTCT
1451       1464
TTCCTGGCAA TTGA
```

FIGURE 14

```
          GCGCCGGTGATGCCGGCCACGATGCGTCCGGCGTAGAGGATCGAGATCTCGATCCCGCGA
     4921 ---------+---------+---------+---------+---------+---------+ 4980
          CGCGGCCACTACGGCCGGTGCTACGCAGGCCGCATCTCCTAGCTCTAGAGCTAGGGCGCT

c          A  G  D  A  G  H  D  A  S  G  V  E  D  R  D  L  D  P  A  K -
              T7 Promoter
          AAT[TAATACGACTCACTATA]GGGGAATTGTGAGCGGATAACAATTCCCCTCTAGACCACA
     4981 ---------+---------+---------+---------+---------+---------+ 5040
          TTAATTATGCTGAGTGATATCCCCTTAACACTCGCCTATTGTTAAGGGGAGATCTGGTGT

c          L  I  R  L  T  I  G  E  L  *  A  D  N  N  S  P  L  D  H  T -
            Shine-Dalgarno    ProIL18 start
          CCTt[aaggag]gatataacatATGGCTGCTGAACCAGTAGAAGACAATTGCATCAACTTTG
     5041 ---------+---------+---------+---------+---------+---------+ 5100
          GGAattcctcctatattgtaTACCGACGACTTGGTCATCTTCTGTTAACGTAGTTGAAAC

c          L  R  R  I  *  H  M  A  A  E  P  V  E  D  N  C  I  N  F  V -

          TGGCAATGAAATTTATTGACAATACGCTTTACTTTATAGCTGAAGATGATGAAAACCTGG
     5101 ---------+---------+---------+---------+---------+---------+ 5160
          ACCGTTACTTTAAATAACTGTTATGCGAAATGAAATATCGACTTCTACTACTTTTGGACC

c          A  M  K  F  I  D  N  T  L  Y  F  I  A  E  D  D  E  N  L  E -
              Start of mature IL18
          AATCAGATTACTTTGGCAAGCTTGAGAGCAAACTATCGGTCATtCGTAATTTAAATGACC
     5161 ---------+---------+---------+---------+---------+---------+ 5220
          TTAGTCTAATGAAACCGTTCGAACTCTCGTTTGATAGCCAGTAaGCATTAAATTTACTGG

c          S  D  Y  F  G  K  L  E  S  K  L  S  V  I  R  N  L  N  D  Q -

          AGGTCCTATTTATCGACCAAGGGAATCGTCCACTATTCGAGGACATGACAGACAGTGACT
     5221 ---------+---------+---------+---------+---------+---------+ 5280
          TCCAGGATAAATAGCTGGTTCCCTTAGCAGGTGATAAGCTCCTGTACTGTCTGTCACTGA

c          V  L  F  I  D  Q  G  N  R  P  L  F  E  D  M  T  D  S  D  C -

          GCCGAGACAATGCGCCGCGAACCATtTTCATTATATCTATGTACAAGGATTCTCAGCCGC
     5281 ---------+---------+---------+---------+---------+---------+ 5340
          CGGCTCTGTTACGCGGCGCTTGGTAaAAGTAATATAGATACATGTTCCTAAGAGTCGGCG

c          R  D  N  A  P  R  T  I  F  I  I  S  M  Y  K  D  S  Q  P  R -
```

FIGURE 14 (continued)

```
          GCGGAATGGCCGTAACTATTTCTGTCAAATGTGAAAAGATATCCACGCTGTCGTGTGAGA
     5341 ---------+---------+---------+---------+---------+---------+ 5400
          CGCCTTACCGGCATTGATAAAGACAGTTTACACTTTTCTATAGGTGCGACAGCACACTCT
c          G  M  A  V  T  I  S  V  K  C  E  K  I  S  T  L  S  C  E  N -

          ACAAgATtATtAGTTTCAAAGAGATGAATCCGCCGGATAATATCAAGGACACGAAGTCTG
     5401 ---------+---------+---------+---------+---------+---------+ 5460
          TGTTcTAaTAaTCAAAGTTTCTCTACTTAGGCGGCCTATTATAGTTCCTGTGCTTCAGAC

c          K  I  I  S  F  K  E  M  N  P  P  D  N  I  K  D  T  K  S  D -

          ATATCATATTTTTCCAGCGCAGCGTGCCGGGGCACGATAACAAGATGCAATTTGAATCAT
     5461 ---------+---------+---------+---------+---------+---------+ 5520
          TATAGTATAAAAAGGTCGCGTCGCACGGCCCCGTGCTATTGTTCTACGTTAAACTTAGTA

c          I  I  F  F  Q  R  S  V  P  G  H  D  N  K  M  Q  F  E  S  S -

          CCAGCTATGAAGGGTACTTTCTTGCATGCGAGAAGGAACGCGATCTCTTTAAACTTATTT
     5521 ---------+---------+---------+---------+---------+---------+ 5580
          GGTCGATACTTCCCATGAAAGAACGTACGCTCTTCCTTGCGCTAGAGAAATTTGAATAAA

c          S  Y  E  G  Y  F  L  A  C  E  K  E  R  D  L  F  K  L  I  L -

          TAAAGAAAGAGGACGAGCTAGGCGATCGCAGCATtATGTTCACTGTCCAAAATGAAGACT
     5581 ---------+---------+---------+---------+---------+---------+ 5640
          ATTTCTTTCTCCTGCTCGATCCGCTAGCGTCGTAaTACAAGTGACAGGTTTTACTTCTGA

c          K  K  E  D  E  L  G  D  R  S  I  M  F  T  V  Q  N  E  D  * -
                Defective Shine-Dalgarno   Start Caspase 5
          AGTggaggatataaTACCAgGaataaataaaatccatgGgccatcatcatcatcatcatg
     5641 ---------+---------+---------+---------+---------+---------+ 5700
          TCAcctcctatattATGGTcCttatttattttaggtacCcggtagtagtagtagtagtac

c          W  R  I  *  Y  Q  E  *  I  K  S  M  G  H  H  H  H  H  H  G -

          gcATACTCAAACTTTGTCCTCGTGAAGAATTCCTGAGACTGTGTAAAAAAAATCATGATG
     5701 ---------+---------+---------+---------+---------+---------+ 5760
          cgTATGAGTTTGAAACAGGAGCACTTCTTAAGGACTCTGACACATTTTTTTTAGTACTAC

c          I  L  K  L  C  P  R  E  E  F  L  R  L  C  K  K  N  H  D  E -

          AGATCTATCCAATAAAAAAGAGAGAGGACCGCAGACGCCTGGCTCTCATCATATGCAATA
     5761 ---------+---------+---------+---------+---------+---------+ 5820
          TCTAGATAGGTTATTTTTTCTCTCTCCTGGCGTCTGCGGACCGAGAGTAGTATACGTTAT

c          I  Y  P  I  K  K  R  E  D  R  R  R  L  A  L  I  I  C  N  T -
```

FIGURE 14 (continued)

```
            CAAAGTTTGATCACCTGCCTGCAAGGAATGGGGCTCACTATGACATCGTGGGGATGAAAA
       5821 ---------+---------+---------+---------+---------+---------+ 5880
            GTTTCAAACTAGTGGACGGACGTTCCTTACCCCGAGTGATACTGTAGCACCCCTACTTTT

c             K  F  D  H  L  P  A  R  N  G  A  H  Y  D  I  V  G  M  K  R -

            GGCTGCTTCAAGGCCTGGGCTACACTGTGGTTGACGAAAAGAATCTCACAGCCAGGGATA
       5881 ---------+---------+---------+---------+---------+---------+ 5940
            CCGACGAAGTTCCGGACCCGATGTGACACCAACTGCTTTTCTTAGAGTGTCGGTCCCTAT

c             L  L  Q  G  L  G  Y  T  V  V  D  E  K  N  L  T  A  R  D  M -

            TGGAGTCAGTGCTGAGGGCATTTGCTGCCAGACCAGAGCACAAGTCCTCTGACAGCACGT
       5941 ---------+---------+---------+---------+---------+---------+ 6000
            ACCTCAGTCACGACTCCCGTAAACGACGGTCTGGTCTCGTGTTCAGGAGACTGTCGTGCA

c             E  S  V  L  R  A  F  A  A  R  P  E  H  K  S  S  D  S  T  F -

            TCTTGGTACTCATGTCTCATGGCATCCTAGAGGGAATCTGCGGAACTGCGCATAAAAAGA
       6001 ---------+---------+---------+---------+---------+---------+ 6060
            AGAACCATGAGTACAGAGTACCGTAGGATCTCCCTTAGACGCCTTGACGCGTATTTTTCT

c             L  V  L  M  S  H  G  I  L  E  G  I  C  G  T  A  H  K  K  K -

            AAAAACCGGATGTGCTGCTTTATGACACCATCTTCCAGATATTCAACAACCGCAACTGCC
       6061 ---------+---------+---------+---------+---------+---------+ 6120
            TTTTTGGCCTACACGACGAAATACTGTGGTAGAAGGTCTATAAGTTGTTGGCGTTGACGG

c             K  P  D  V  L  L  Y  D  T  I  F  Q  I  F  N  N  R  N  C  L -

            TCAGTCTAAAGGACAAACCCAAGGTCATCATTGTCCAGGCCTGCAGAGGTGAAAAACATG
       6121 ---------+---------+---------+---------+---------+---------+ 6180
            AGTCAGATTTCCTGTTTGGGTTCCAGTAGTAACAGGTCCGGACGTCTCCACTTTTTGTAC

c             S  L  K  D  K  P  K  V  I  I  V  Q  A  C  R  G  E  K  H  G -

            GGGAACTCTGGGTCAGAGACTCTCCAGCATCCTTGGCAGTCATCTCTTCACAGTCATCTG
       6181 ---------+---------+---------+---------+---------+---------+ 6240
            CCCTTGAGACCCAGTCTCTGAGAGGTCGTAGGAACCGTCAGTAGAGAAGTGTCAGTAGAC

c             E  L  W  V  R  D  S  P  A  S  L  A  V  I  S  S  Q  S  S  E -

            AGAACCTGGAGGCAGATTCTGTTTGCAAGATCCACGAGGAGAAGGACTTCATTGCTTTCT
       6241 ---------+---------+---------+---------+---------+---------+ 6300
            TCTTGGACCTCCGTCTAAGACAAACGTTCTAGGTGCTCCTCTTCCTGAAGTAACGAAAGA

c             N  L  E  A  D  S  V  C  K  I  H  E  E  K  D  F  I  A  F  C -
```

FIGURE 14 (continued)

```
        GTTCTTCAACACCACATAACGTGTCCTGGAGAGACCGCACAAGGGGCTCCATCTTCATTA
   6301 ---------+---------+---------+---------+---------+---------+ 6360
        CAAGAAGTTGTGGTGTATTGCACAGGACCTCTCTGGCGTGTTCCCCGAGGTAGAAGTAAT

c         S  S  T  P  H  N  V  S  W  R  D  R  T  R  G  S  I  F  I  T -

        CGGAACTCATCACATGCTTCCAGAAATATTCTTGCTGCTGCCACCTAATGGAAATATTTC
   6361 ---------+---------+---------+---------+---------+---------+ 6420
        GCCTTGAGTAGTGTACGAAGGTCTTTATAAGAACGACGACGGTGGATTACCTTTATAAAG

c         E  L  I  T  C  F  Q  K  Y  S  C  C  C  H  L  M  E  I  F  R -

        GGAAGGTACAGAAATCATTTGAAGTTCCACAGGCTAAAGCCCAGATGCCCACCATAGAAC
   6421 ---------+---------+---------+---------+---------+---------+ 6480
        CCTTCCATGTCTTTAGTAAACTTCAAGGTGTCCGATTTCGGGTCTACGGGTGGTATCTTG

c         K  V  Q  K  S  F  E  V  P  Q  A  K  A  Q  M  P  T  I  E  R -

        GAGCAACCTTGACAAGAGATTTCTACCTCTTTCCTGGCAATTGACTCGAGCACCACCACC
   6481 ---------+---------+---------+---------+---------+---------+ 6540
        CTCGTTGGAACTGTTCTCTAAAGATGGAGAAAGGACCGTTAACTGAGCTCGTGGTGGTGG

c         A  T  L  T  R  D  F  Y  L  F  P  G  N  *  L  E  H  H  H  H -

        ACCACCACTGAGATCCGGCTGCTAACAAAGCCCGAAAGGAAGCTGAGTTGGCTGCTGCCA
   6541 ---------+---------+---------+---------+---------+---------+ 6600
        TGGTGGTGACTCTAGGCCGACGATTGTTTCGGGCTTTCCTTCGACTCAACCGACGACGGT

c         H  H  *  D  P  A  A  N  K  A  R  K  E  A  E  L  A  A  A  T -
                                                 T7 Terminator
        CCGCTGAGCAATAACTAGCATAACCCCTTGGGGCCTCTAAACGGGTCTTGAGGGGTTTTT
   6601 ---------+---------+---------+---------+---------+---------+ 6660
        GGCGACTCGTTATTGATCGTATTGGGGAACCCCGGAGATTTGCCCAGAACTCCCCAAAAA

c         A  E  Q  *  L  A  *  P  L  G  A  S  K  R  V  L  R  G  F  L -

        TGCTGAAAGGAGGAACTATATCCGGT
   6661 ---------+---------+------- 6687
        ACGACTTTCCTCCTTGATATAGGCCA

c         L  K  G  G  T  I  S  G   -
```

FIGURE 16

SEQ ID NO:10

```
1   MQIFVKTLTG KTITLEVESS DTIDNVKSKI QDKEGIPPDQ QRLIFAGKQL
51  EDGRTLSDYN IQKESTLHLV LRLRGGYFGK LESKLSVIRN LNDQVLFIDQ
101 GNRPLFEDMT DSDCRDNAPR TIFIISMYKD SQPRGMAVTI SVKCEKISTL
151 SCENKIISFK EMNPPDNIKD TKSDIIFFQR SVPGHDNKMQ FESSSYEGYF
201 LACEKERDLF KLILKKEDEL GDRSIMFTVQ NED
```

FIGURE 17

SEQ ID NO:11

```
1                                                    50
ATGCAGATCT TCGTCAAGAC GTTAACCGGT AAAACCATAA CTCTAGAAGT
51                                                  100
TGAATCTTCC GATACCATCG ACAACGTTAA GTCGAAAATT CAAGACAAGG
101                                                 150
AAGGCATTCC ACCTGATCAA CAAAGATTGA TCTTTGCCGG TAAGCAGCTC
151                                                 200
GAAGACGGTA GAACGCTGTC TGATTACAAC ATTCAGAAGG AGTCGACCTT
201                                                 250
ACATCTTGTC TTAAGACTAA GAGGAGGGTA CTTTGGCAAG CTTGAGAGCA
251                                                 300
AACTATCGGT CATTCGTAAT TTAAATGACC AGGTCCTATT TATCGACCAA
301                                                 350
GGGAATCGTC CACTATTCGA GGACATGACA GACAGTGACT GCCGAGACAA
351                                                 400
TGCGCCGCGA ACCATTTTCA TTATATCTAT GTACAAGGAT TCTCAGCCGC
401                                                 450
GCGGAATGGC CGTAACTATT TCTGTCAAAT GTGAAAAGAT ATCCACGCTG
451                                                 500
TCGTGTGAGA ACAAGATTAT TAGTTTCAAA GAGATGAATC CGCCGGATAA
501                                                 550
TATCAAGGAC ACGAAGTCTG ATATCATATT TTTCCAGCGC AGCGTGCCGG
551                                                 600
GGCACGATAA CAAGATGCAA TTTGAATCAT CCAGCTATGA AGGGTACTTT
601                                                 650
CTTGCATGCG AGAAGGAACG CGATCTCTTT AAACTTATTT TAAAGAAAGA
651                                                 700
GGACGAGCTA GGCGATCGCA GCATTATGTT CACTGTCCAA AATGAAGACT
701
AG
```

FIGURE 18

SEQ ID NO:12

```
1                                                  50
AGATCTCGAT CCCGCGAAAT TAATACGACT CACTATAGGG GAATTGTGAG
51                                                100
CGGATAACAA TTCCCCTCTA GACCACACCT TAAGGAGGAT ATAACATATG
101                                               150
CAGATCTTCG TCAAGACGTT AACCGGTAAA ACCATAACTC TAGAAGTTGA
151                                               200
ATCTTCCGAT ACCATCGACA ACGTTAAGTC GAAAATTCAA GACAAGGAAG
201                                               250
GCATTCCACC TGATCAACAA AGATTGATCT TTGCCGGTAA GCAGCTCGAG
251                                               300
GACGGTAGAA CGCTGTCTGA TTACAACATT CAGAAGGAGT CGACCTTACA
301                                               350
TCTTGTCTTA AGACTAAGAG GAGGGTACTT TGGCAAGCTT GAGAGCAAAC
351                                               400
TATCGGTCAT TCGTAATTTA AATGACCAGG TCCTATTTAT CGACCAAGGG
401                                               450
AATCGTCCAC TATTCGAGGA CATGACAGAC AGTGACTGCC GAGACAATGC
451                                               500
GCCGCGAACC ATTTTCATTA TATCTATGTA CAAGGATTCT CAGCCGCGCG
501                                               550
GAATGGCCGT AACTATTTCT GTCAAATGTG AAAAGATATC CACGCTGTCG
551                                               600
TGTGAGAACA AGATTATTAG TTTCAAAGAG ATGAATCCGC CGGATAATAT
601                                               650
CAAGGACACG AAGTCTGATA TCATATTTTT CCAGCGCAGC GTGCCGGGGC
651                                               700
ACGATAACAA GATGCAATTT GAATCATCCA GCTATGAAGG GTACTTTCTT
701                                               750
GCATGCGAGA AGGAACGCGA TCTCTTTAAA CTTATTTTAA AGAAAGAGGA
751                                               800
CGAGCTAGGC GATCGCAGCA TTATGTTCAC TGTCCAAAAT GAAGACTAGT
801                                               850
GGAGGATATA ATACCAGGAA TAAATAAAAT CCATGGGCCA TCATCATCAT
851                                               900
CATCATGGCA TGGATGAAAG CAAGATAAAC AGTTTATTAC AATTTTTATT
901                                               950
TGGTTCCCGA CAGGATTTTT TGAGAAATTT TAAAACTTGG AGTAACAACA
```

FIGURE 18 (continued)

951 1000
ATAACAATCT ATCGATTTAT TTATTAATTT TTGGCATAGT AGTATTTTTT
1001 1050
TATAAAAAAC CAGACCATCT AAACTACATT GTTGAGAGCG TTAGTGAAAT
1051 1100
GACAACAAAC TTCAGAAATA ATAATAGCCT TAGCCGTTGG TTGCCCAGAA
1101 1150
GTAAGTTTAC CCACTTAGAC GAAGAGATCT TGAAAAGAGG TGGTTTCATT
1151 1200
GCTGGTTTAG TTAATGATGG TAACACTTGT TTTATGAACT CTGTTTTGCA
1201 1250
ATCATTGGCA TCATCCAGAG AATTAATGGA GTTCTTGGAC AATAATGTCA
1251 1300
TAAGGACCTA TGAGGAGATA GAACAAAATG AACACAATGA AGAAGGAAAC
1301 1350
GGGCAAGAAT CTGCTCAAGA TGAAGCCACT CATAAGAAAA ACACTCGTAA
1351 1400
GGGTGGCAAA GTTTATGGTA AGCATAAGAA GAAATTGAAT AGGAAGTCAA
1401 1450
GTTCGAAAGA AGACGAAGAA AAGAGCCAGG AGCCAGATAT CACTTTCAGT
1451 1500
GTCGCCTTAA GGGATCTACT TTCTGCCTTA AATGCGAAGT ATTATCGGGA
1501 1550
TAAACCCTAT TTCAAAACCA ATAGTTTATT GAAAGCAATG TCCAAATCTC
1551 1600
CAAGAAAAAA TATTCTTCTT GGCTACGACC AAGAGGACGC GCAAGAATTC
1601 1650
TTCCAGAACA TACTAGCCGA GTTGGAAAGT AACGTTAAAT CATTGAATAC
1651 1700
TGAAAAACTA GATACCACTC CAGTTGCGAA ATCAGAATTA CCCGATGATG
1701 1750
CTTTAGTAGG TCAACTTAAC CTTGGTGAAG TTGGCACTGT TTACATTCCA
1751 1800
ACTGAACAGA TTGATCCTAA CTCTATACTA CATGACAAGT CCATTCAAAA
1801 1850
TTTCACACCT TTCAAACTAA TGACTCCTTT AGATGGTATC ACGGCAGAAA
1851 1900
GAATTGGTTG TTTACAGTGT GGTGAGAACG GTGGCATAAG ATATTCCGTA
1901 1950
TTTTCGGGAT TAAGCTTAAA TTTACCGAAC GAGAATATTG GTTCCACTTT

FIGURE 18 (continued)

1951 2000
AAAATTATCT CAGTTATTGA GCGACTGGAG TAAACCTGAA ATCATCGAAG
2001 2050
TCGTAGAATG TAACCGTTGT GCCCTCACAG CAGCGCACTC TCATTTATTT
2051 2100
GGTCAGTTGA AAGAATTTGA AAAAAAACCT GAGGGTTCGA TCCCAGAAAA
2101 2150
GCCAATTAAC GCTGTAAAAG ATAGGGTCCA TCAAATCGAA GAAGTTCTTG
2151 2200
CCAAACCAGT TATTGACGAT GAAGATTATA AGAAGTTGCA TACAGCAAAT
2201 2250
ATGGTACGTA AATGCTCTAA ATCTAAGCAG ATTTTAATAT CAAGACCTCC
2251 2300
ACCATTATTA TCCATTCATA TCAACAGATC CGTATTTGAT CCAAGAACGT
2301 2350
ACATGATTAG AAAAAATAAC TCGAAAGTAT TGTTTAAGTC AACGTTGAAT
2351 2400
CTTGCCCCTT GGTGTTGTGA TATTAATGAA ATCAATTTGG ATGCTCGTTT
2401 2450
GCCAATGTCA AAAAAGGAAA AAGCTGCGCA ACAAGATTCA AGTGAAGATG
2451 2500
AAAACATTGG CGGTGAATAC TATACGAAAT TACATGAACG CTTCGAGCAG
2501 2550
GAATTTGAAG ACAGCGAGGA AGAAAAAGAA TACGATGACG CAGAGGGGAA
2551 2600
CTATGCGTCT CATTACAATC ATACCAAGGA TATCAGTAAC TATGATCCCC
2601 2650
TAAACGGTGA AGTCGATGGC GTGACATCCG ATGATGAAGA TGAGTACATT
2651 2700
GAAGAAACCG ATGCTTTAGG GAATACAATC AAAAAAAGGA TCATAGAACA
2701 2750
TTCTGATGTT GAAAACGAGA ATGTAAAAGA TAATGAAGAA CTGCAAGAAA
2751 2800
TCGACAATGT GAGCCTTGAC GAACCAAAGA TCAATGTTGA AGATCAACTA
2801 2850
GAAACATCAT CTGATGAGGA AGATGTTATA CCAGCTCCAC CTATCAATTA
2851 2900
TGCTAGGTCA TTTTCCACAG TTCCAGCCAC TCCATTGACA TATTCATTGC
2901 2950
GCTCTGTCAT TGTTCACTAC GGTACCCATA ATTATGGTCA TTACATTGCA

FIGURE 18 (continued)

2951 3000
TTTAGAAAAT ACAGGGGTTG TTGGTGGAGA ATATCTGATG AGACTGTGTA
3001 3050
CGTTGTGGAC GAAGCTGAAG TCCTTTCAAC ACCCGGTGTA TTTATGTTAT
3051 3100
TTTACGAATA TGACTTTGAT GAAGAAACTG GGAAGATGAA GGATGATTTG
3101 3150
GAAGCTATTC AGAGTAATAA TGAAGAAGAT GATGAAAAAG AGCAGGAGCA
3151 3200
AAAAGGAGTC CAGGAGCCAA AGGAAAGCCA AGAGCAAGGA GAAGGTGAAG
3201 3250
AGCAAGAGGA AGGTCAAGAG CAGATGAAGT TCGAGAGAAC AGAAGACCAT
3251 3300
AGAGATATTT CTGGTAAAGA TGTAAACTAA GCTCGAGCAC CACCACCACC
3301 3350
ACCACTGAGA TCCGGCTGCT AACAAAGCCC GAAAGGAAGC TGAGTTGGCT
3351 3400
GCTGCCACCG CTGAGCAATA ACTAGCATAA CCCCTTGGGG CCTCTAAACG
3401 3419
GGTCTTGAGG GGTTTTTTG

FIGURE 19

```
                               T7 Promoter
     AGATCTCGATCCCGCGAAATTAATACGACTCACTATAGGGGAATTGTGAGCGGATAACAA
4964 ------+---------+---------+---------+---------+---------+--- 5023
     TCTAGAGCTAGGGCGCTTTAATTATGCTGAGTGATATCCCCTTAACACTCGCCTATTGTT

                         Shine-Dalgarno     Start of Ub-IL18
     TTCCCCTCTAGACCACACCTTaaggaggatataacatATGCAGATCTTCGTCAAGACGTT
5024 ------+---------+---------+---------+---------+---------+--- 5083
     AAGGGGAGATCTGGTGTGGAattcctcctatattgtaTACGTCTAGAAGCAGTTCTGCAA

b                                          M  Q  I  F  V  K  T  L  -

     AACCGGTAAAACCATAACTCTAGAAGTTGAATCTTCCGATACCATCGACAACGTTAAGTC
5084 ------+---------+---------+---------+---------+---------+--- 5143
     TTGGCCATTTTGGTATTGAGATCTTCAACTTAGAAGGCTATGGTAGCTGTTGCAATTCAG

b      T  G  K  T  I  T  L  E  V  E  S  S  D  T  I  D  N  V  K  S  -

     GAAAATTCAAGACAAGGAAGGCATTCCACCTGATCAACAAAGATTGATCTTTGCCGGTAA
5144 ------+---------+---------+---------+---------+---------+--- 5203
     CTTTTAAGTTCTGTTCCTTCCGTAAGGTGGACTAGTTGTTTCTAACTAGAAACGGCCATT

b      K  I  Q  D  K  E  G  I  P  P  D  Q  Q  R  L  I  F  A  G  K  -

     GCAGCTCGAGGACGGTAGAACGCTGTCTGATTACAACATTCAGAAGGAGTCGACCTTACA
5204 ------+---------+---------+---------+---------+---------+--- 5263
     CGTCGAGCTCCTGCCATCTTGCGACAGACTAATGTTGTAAGTCTTCCTCAGCTGGAATGT

b      Q  L  E  D  G  R  T  L  S  D  Y  N  I  Q  K  E  S  T  L  H  -
                                Start of mature IL18
     TCTTGTcTTAAGACTAAGAGGAGGGTACTTTGGCAAGCTTGAGAGCAAACTATCGGTCAT
5264 ------+---------+---------+---------+---------+---------+--- 5323
     AGAACAgAATTCTGATTCTCCTCCCATGAAACCGTTCGAACTCTCGTTTGATAGCCAGTA

b      L  V  L  R  L  R  G  G  Y  F  G  K  L  E  S  K  L  S  V  I  -
```

FIGURE 19 (continued)

```
        tCGTAATTTAAATGACCAGGTCCTATTTATCGACCAAGGGAATCGTCCACTATTCGAGGA
   5324 ------+---------+---------+---------+---------+---------+--- 5383
        aGCATTAAATTTACTGGTCCAGGATAAATAGCTGGTTCCCTTAGCAGGTGATAAGCTCCT

b        R  N  L  N  D  Q  V  L  F  I  D  Q  G  N  R  P  L  F  E  D  -

        CATGACAGACAGTGACTGCCGAGACAATGCGCCGCGAACCATtTTCATTATATCTATGTA
   5384 ------+---------+---------+---------+---------+---------+--- 5443
        GTACTGTCTGTCACTGACGGCTCTGTTACGCGGCGCTTGGTAaAAGTAATATAGATACAT

b        M  T  D  S  D  C  R  D  N  A  P  R  T  I  F  I  I  S  M  Y  -

        CAAGGATTCTCAGCCGCGCGGAATGGCCGTAACTATTTCTGTCAAATGTGAAAAGATATC
   5444 ------+---------+---------+---------+---------+---------+--- 5503
        GTTCCTAAGAGTCGGCGCGCCTTACCGGCATTGATAAAGACAGTTTACACTTTTCTATAG

b        K  D  S  Q  P  R  G  M  A  V  T  I  S  V  K  C  E  K  I  S  -

        CACGCTGTCGTGTGAGAACAAgATtATtAGTTTCAAAGAGATGAATCCGCCGGATAATAT
   5504 ------+---------+---------+---------+---------+---------+--- 5563
        GTGCGACAGCACACTCTTGTTcTAaTAaTCAAAGTTTCTCTACTTAGGCGGCCTATTATA

b        T  L  S  C  E  N  K  I  I  S  F  K  E  M  N  P  P  D  N  I  -

        CAAGGACACGAAGTCTGATATCATATTTTTCCAGCGCAGCGTGCCGGGGCACGATAACAA
   5564 ------+---------+---------+---------+---------+---------+--- 5623
        GTTCCTGTGCTTCAGACTATAGTATAAAAAGGTCGCGTCGCACGGCCCCGTGCTATTGTT

b        K  D  T  K  S  D  I  I  F  F  Q  R  S  V  P  G  H  D  N  K  -

        GATGCAATTTGAATCATCCAGCTATGAAGGGTACTTTCTTGCATGCGAGAAGGAACGCGA
   5624 ------+---------+---------+---------+---------+---------+--- 5683
        CTACGTTAAACTTAGTAGGTCGATACTTCCCATGAAAGAACGTACGCTCTTCCTTGCGCT

b        M  Q  F  E  S  S  S  Y  E  G  Y  F  L  A  C  E  K  E  R  D  -

        TCTCTTTAAACTTATTTTAAAGAAAGAGGACGAGCTAGGCGATCGCAGCATtATGTTCAC
   5684 ------+---------+---------+---------+---------+---------+--- 5743
        AGAGAAATTTGAATAAAATTTCTTTCTCCTGCTCGATCCGCTAGCGTCGTAaTACAAGTG
```

FIGURE 19 (continued)

```
b          L  F  K  L  I  L  K  K  E  D  E  L  G  D  R  S  I  M  F  T  -
                                   Defective Shine-Dalgarno    Start of Upb-1
          TGTCCAAAATGAAGACTAGTggaggatataaTACCAgGaataaataaaatccatgggcca
    5744  ------+---------+---------+---------+---------+---------+--- 5803
          ACAGGTTTTACTTCTGATCAcctcctatattATGGTcCttatttattttaggtacccggt

b          V  Q  N  E  D  *                                M  G  H  -

          tcatcatcatcatcatggcATGGATGAAAGCAAGATAAACAGTTTATTACAATTTTTATT
    5804  ------+---------+---------+---------+---------+---------+--- 5863
          agtagtagtagtagtaccgTACCTACTTTCGTTCTATTTGTCAAATAATGTTAAAAATAA

b          H  H  H  H  H  G  M  D  E  S  K  I  N  S  L  L  Q  F  L  F  -

          TGGTTCCCGACAGGATTTTTTGAGAAATTTTAAAACTTGGAGTAACAACAATAACAATCT
    5864  ------+---------+---------+---------+---------+---------+--- 5923
          ACCAAGGGCTGTCCTAAAAAACTCTTTAAAATTTTGAACCTCATTGTTGTTATTGTTAGA

b          G  S  R  Q  D  F  L  R  N  F  K  T  W  S  N  N  N  N  N  L  -

          ATCGATTTATTTATTAATTTTTGGCATAGTAGTATTTTTTTATAAAAAACCAGACCATCT
    5924  ------+---------+---------+---------+---------+---------+--- 5983
          TAGCTAAATAAATAATTAAAAACCGTATCATCATAAAAAAATATTTTTTGGTCTGGTAGA

b          S  I  Y  L  L  I  F  G  I  V  V  F  F  Y  K  K  P  D  H  L  -

          AAACTACATTGTTGAGAGCGTTAGTGAAATGACAACAAACTTCAGAAATAATAATAGCCT
    5984  ------+---------+---------+---------+---------+---------+--- 6043
          TTTGATGTAACAACTCTCGCAATCACTTTACTGTTGTTTGAAGTCTTTATTATTATCGGA

b          N  Y  I  V  E  S  V  S  E  M  T  T  N  F  R  N  N  N  S  L  -

          TAGCCGTTGGTTGCCCAGAAGTAAGTTTACCCACTTAGACGAAGAGATCTTGAAAAGAGG
    6044  ------+---------+---------+---------+---------+---------+--- 6103
          ATCGGCAACCAACGGGTCTTCATTCAAATGGGTGAATCTGCTTCTCTAGAACTTTTCTCC

b          S  R  W  L  P  R  S  K  F  T  H  L  D  E  E  I  L  K  R  G  -

          TGGTTTCATTGCTGGTTTAGTTAATGATGGTAACACTTGTTTTATGAACTCTGTTTTGCA
    6104  ------+---------+---------+---------+---------+---------+--- 6163
```

FIGURE 19 (continued)

```
        ACCAAAGTAACGACCAAATCAATTACTACCATTGTGAACAAAATACTTGAGACAAAACGT

b        G  F  I  A  G  L  V  N  D  G  N  T  C  F  M  N  S  V  L  Q  -

ATCATTGGCATCATCCAGAGAATTAATGGAGTTCTTGGACAATAATGTCATAAGGACCTA
   6164 ------+---------+---------+---------+---------+---------+--- 6223
        TAGTAACCGTAGTAGGTCTCTTAATTACCTCAAGAACCTGTTATTACAGTATTCCTGGAT

b        S  L  A  S  S  R  E  L  M  E  F  L  D  N  N  V  I  R  T  Y  -

        TGAGGAGATAGAACAAAATGAACACAATGAAGAAGGAAACGGGCAAGAATCTGCTCAAGA
   6224 ------+---------+---------+---------+---------+---------+--- 6283
        ACTCCTCTATCTTGTTTTACTTGTGTTACTTCTTCCTTTGCCCGTTCTTAGACGAGTTCT

b        E  E  I  E  Q  N  E  H  N  E  E  G  N  G  Q  E  S  A  Q  D  -

        TGAAGCCACTCATAAGAAAAACACTCGTAAGGGTGGCAAAGTTTATGGTAAGCATAAGAA
   6284 ------+---------+---------+---------+---------+---------+--- 6343
        ACTTCGGTGAGTATTCTTTTTGTGAGCATTCCCACCGTTTCAAATACCATTCGTATTCTT

b        E  A  T  H  K  K  N  T  R  K  G  G  K  V  Y  G  K  H  K  K  -

        GAAATTGAATAGGAAGTCAAGTTCGAAAGAAGACGAAGAAAAGAGCCAGGAGCCAGATAT
   6344 ------+---------+---------+---------+---------+---------+--- 6403
        CTTTAACTTATCCTTCAGTTCAAGCTTTCTTCTGCTTCTTTTCTCGGTCCTCGGTCTATA

b        K  L  N  R  K  S  S  S  K  E  D  E  E  K  S  Q  E  P  D  I  -

        CACTTTCAGTGTCGCCTTAAGGGATCTACTTTCTGCCTTAAATGCGAAGTATTATCGGGA
   6404 ------+---------+---------+---------+---------+---------+--- 6463
        GTGAAAGTCACAGCGGAATTCCCTAGATGAAAGACGGAATTTACGCTTCATAATAGCCCT

b        T  F  S  V  A  L  R  D  L  L  S  A  L  N  A  K  Y  Y  R  D  -

        TAAACCCTATTTCAAAACCAATAGTTTATTGAAAGCAATGTCCAAATCTCCAAGAAAAAA
   6464 ------+---------+---------+---------+---------+---------+--- 6523
        ATTTGGGATAAAGTTTTGGTTATCAAATAACTTTCGTTACAGGTTTAGAGGTTCTTTTTT

b        K  P  Y  F  K  T  N  S  L  L  K  A  M  S  K  S  P  R  K  N  -

        TATTCTTCTTGGCTACGACCAAGAGGACGCGCAAGAATTCTTCCAGAACATACTAGCCGA
```

FIGURE 19 (continued)

```
6524 ------+---------+---------+---------+---------+---------+--- 6583
     ATAAGAAGAACCGATGCTGGTTCTCCTGCGCGTTCTTAAGAAGGTCTTGTATGATCGGCT

b     I  L  L  G  Y  D  Q  E  D  A  Q  E  F  F  Q  N  I  L  A  E  -
     GTTGGAAAGTAACGTTAAATCATTGAATACTGAAAAACTAGATACCACTCCAGTTGCGAA
6584 ------+---------+---------+---------+---------+---------+--- 6643
     CAACCTTTCATTGCAATTTAGTAACTTATGACTTTTTGATCTATGGTGAGGTCAACGCTT

b     L  E  S  N  V  K  S  L  N  T  E  K  L  D  T  T  P  V  A  K  -

     ATCAGAATTACCCGATGATGCTTTAGTAGGTCAACTTAACCTTGGTGAAGTTGGCACTGT
6644 ------+---------+---------+---------+---------+---------+--- 6703
     TAGTCTTAATGGGCTACTACGAAATCATCCAGTTGAATTGGAACCACTTCAACCGTGACA

b     S  E  L  P  D  D  A  L  V  G  Q  L  N  L  G  E  V  G  T  V  -

     TTACATTCCAACTGAACAGATTGATCCTAACTCTATACTACATGACAAGTCCATTCAAAA
6704 ------+---------+---------+---------+---------+---------+--- 6763
     AATGTAAGGTTGACTTGTCTAACTAGGATTGAGATATGATGTACTGTTCAGGTAAGTTTT

b     Y  I  P  T  E  Q  I  D  P  N  S  I  L  H  D  K  S  I  Q  N  -

     TTTCACACCTTTCAAACTAATGACTCCTTTAGATGGTATCACGGCAGAAAGAATTGGTTG
6764 ------+---------+---------+---------+---------+---------+--- 6823
     AAAGTGTGGAAAGTTTGATTACTGAGGAAATCTACCATAGTGCCGTCTTTCTTAACCAAC

b     F  T  P  F  K  L  M  T  P  L  D  G  I  T  A  E  R  I  G  C  -

     TTTACAGTGTGGTGAGAACGGTGGCATAAGATATTCCGTATTTTCGGGATTAAGCTTAAA
6824 ------+---------+---------+---------+---------+---------+--- 6883
     AAATGTCACACCACTCTTGCCACCGTATTCTATAAGGCATAAAAGCCCTAATTCGAATTT

b     L  Q  C  G  E  N  G  G  I  R  Y  S  V  F  S  G  L  S  L  N  -

     TTTACCGAACGAGAATATTGGTTCCACTTTAAAATTATCTCAGTTATTgAGCGACTGGAG
6884 ------+---------+---------+---------+---------+---------+--- 6943
     AAATGGCTTGCTCTTATAACCAAGGTGAAATTTTAATAGAGTCAATAAcTCGCTGACCTC

b     L  P  N  E  N  I  G  S  T  L  K  L  S  Q  L  L  S  D  W  S  -
```

FIGURE 19 (continued)

```
         TAAACCTGAAATCATCGAAGTCGTAGAATGTAACCGTTGTGCCCTCACAGCAGCGCACTC
    6944 ------+---------+---------+---------+---------+---------+--- 7003
         ATTTGGACTTTAGTAGCTTCAGCATCTTACATTGGCAACACGGGAGTGTCGTCGCGTGAG

b          K  P  E  I  I  E  V  V  E  C  N  R  C  A  L  T  A  A  H  S  -

TCATTTATTTGGTCAGTTGAAAGAATTTGAAAAAAAACCTGAGGGTTCGATCCCAGAAAA
    7004 ------+---------+---------+---------+---------+---------+--- 7063
         AGTAAATAAACCAGTCAACTTTCTTAAACTTTTTTTTGGACTCCCAAGCTAGGGTCTTTT

b          H  L  F  G  Q  L  K  E  F  E  K  K  P  E  G  S  I  P  E  K  -

         GCCAATTAACGCTGTAAAAGATAGGGTCCATCAAATCGAAGAAGTTCTTGCCAAACCAGT
    7064 ------+---------+---------+---------+---------+---------+--- 7123
         CGGTTAATTGCGACATTTTCTATCCCAGGTAGTTTAGCTTCTTCAAGAACGGTTTGGTCA

b          P  I  N  A  V  K  D  R  V  H  Q  I  E  E  V  L  A  K  P  V  -

         TATTGACGATGAAGATTATAAGAAGTTGCATACAGCAAATATGGTACGTAAATGCTCTAA
    7124 ------+---------+---------+---------+---------+---------+--- 7183
         ATAACTGCTACTTCTAATATTCTTCAACGTATGTCGTTTATACCATGCATTTACGAGATT

b          I  D  D  E  D  Y  K  K  L  H  T  A  N  M  V  R  K  C  S  K  -

         ATCTAAGCAGATTTTAATATCAAGACCTCCACCATTATTATCCATTCATATCAACAGATC
    7184 ------+---------+---------+---------+---------+---------+--- 7243
         TAGATTCGTCTAAAATTATAGTTCTGGAGGTGGTAATAATAGGTAAGTATAGTTGTCTAG

b          S  K  Q  I  L  I  S  R  P  P  P  L  L  S  I  H  I  N  R  S  -

         CGTATTTGATCCAAGAACGTACATGATTAGAAAAAATAACTCGAAAGTATTGTTTAAGTC
    7244 ------+---------+---------+---------+---------+---------+--- 7303
         GCATAAACTAGGTTCTTGCATGTACTAATCTTTTTTATTGAGCTTTCATAACAAATTCAG

b          V  F  D  P  R  T  Y  M  I  R  K  N  N  S  K  V  L  F  K  S  -

         AACGTTGAATCTTGCCCCtTGGTGTTGTGATATTAATGAAATCAATTTGGATGCTCGTTT
    7304 ------+---------+---------+---------+---------+---------+--- 7363
         TTGCAACTTAGAACGGGGaACCACAACACTATAATTACTTTAGTTAAACCTACGAGCAAA

b          T  L  N  L  A  P  W  C  C  D  I  N  E  I  N  L  D  A  R  L  -
```

FIGURE 19 (continued)

```
         GCCAATGTCAAAAAAGGAAAAAGCTGCGCAACAAGATTCAAGTGAAGATGAAAACATTGG
    7364 ------+---------+---------+---------+---------+---------+--- 7423
         CGGTTACAGTTTTTTCCTTTTTCGACGCGTTGTTCTAAGTTCACTTCTACTTTTGTAACC

b         P  M  S  K  K  E  K  A  A  Q  Q  D  S  S  E  D  E  N  I  G  -
CGGTGAATACTATACGAAATTACATGAACGCTTCGAGCAGGAATTTGAAGACAGCGAGGA
    7424 ------+---------+---------+---------+---------+---------+--- 7483
         GCCACTTATGATATGCTTTAATGTACTTGCGAAGCTCGTCCTTAAACTTCTGTCGCTCCT

b         G  E  Y  Y  T  K  L  H  E  R  F  E  Q  E  F  E  D  S  E  E  -

         AGAAAAAGAATACGATGACGCAGAGGGGAACTATGCGTCTCATTACAATCATACCAAGGA
    7484 ------+---------+---------+---------+---------+---------+--- 7543
         TCTTTTTCTTATGCTACTGCGTCTCCCCTTGATACGCAGAGTAATGTTAGTATGGTTCCT

b         E  K  E  Y  D  D  A  E  G  N  Y  A  S  H  Y  N  H  T  K  D  -

         TATCAGTAACTATGATCCCCTAAACGGTGAAGTCGATGGCGTGACATCCGATGATGAAGA
    7544 ------+---------+---------+---------+---------+---------+--- 7603
         ATAGTCATTGATACTAGGGGATTTGCCACTTCAGCTACCGCACTGTAGGCTACTACTTCT

b         I  S  N  Y  D  P  L  N  G  E  V  D  G  V  T  S  D  D  E  D  -

         TGAGTACATTGAAGAAACCGATGCTTTAGGGAATACAATCAAAAAAAGGATCATAGAACA
    7604 ------+---------+---------+---------+---------+---------+--- 7663
         ACTCATGTAACTTCTTTGGCTACGAAATCCCTTATGTTAGTTTTTTTCCTAGTATCTTGT

b         E  Y  I  E  E  T  D  A  L  G  N  T  I  K  K  R  I  I  E  H  -

         TTCTGATGTTGAAAACGAGAATGTAAAAGATAATGAAGAACTGCAAGAAATCGACAATGT
    7664 ------+---------+---------+---------+---------+---------+--- 7723
         AAGACTACAACTTTTGCTCTTACATTTTCTATTACTTCTTGACGTTCTTTAGCTGTTACA

b         S  D  V  E  N  E  N  V  K  D  N  E  E  L  Q  E  I  D  N  V  -

         GAGCCTTGACGAACCAAAGATCAATGTTGAAGATCAACTAGAAACATCATCTGATGAGGA
    7724 ------+---------+---------+---------+---------+---------+--- 7783
         CTCGGAACTGCTTGGTTTCTAGTTACAACTTCTAGTTGATCTTTGTAGTAGACTACTCCT

b         S  L  D  E  P  K  I  N  V  E  D  Q  L  E  T  S  S  D  E  E  -
```

FIGURE 19 (continued)

```
      AGATGTTATACCAGCTCCACCTATCAATTATGCTAGGTCATTTTCCACAGTTCCAGCCAC
 7784 ------+---------+---------+---------+---------+---------+--- 7843
      TCTACAATATGGTCGAGGTGGATAGTTAATACGATCCAGTAAAAGGTGTCAAGGTCGGTG

b      D  V  I  P  A  P  P  I  N  Y  A  R  S  F  S  T  V  P  A  T  -
      TCCATTGACATATTCATTGCGCTCTGTCATTGTTCACTACGGTACCCATAATTATGGTCA
 7844 ------+---------+---------+---------+---------+---------+--- 7903
      AGGTAACTGTATAAGTAACGCGAGACAGTAACAAGTGATGCCATGGGTATTAATACCAGT

b      P  L  T  Y  S  L  R  S  V  I  V  H  Y  G  T  H  N  Y  G  H  -

      TTACATTGCATTTAGAAAATACAGGGGTTGTTGGTGGAGAATATCTGATGAGACTGTGTA
 7904 ------+---------+---------+---------+---------+---------+--- 7963
      AATGTAACGTAAATCTTTTATGTCCCCAACAACCACCTCTTATAGACTACTCTGACACAT

b      Y  I  A  F  R  K  Y  R  G  C  W  W  R  I  S  D  E  T  V  Y  -

      CGTTGTGGACGAAGCTGAAGTCCTTTCAACACCCGGTGTATTTATGTTATTTTACGAATA
 7964 ------+---------+---------+---------+---------+---------+--- 8023
      GCAACACCTGCTTCGACTTCAGGAAAGTTGTGGGCCACATAAATACAATAAAATGCTTAT

b      V  V  D  E  A  E  V  L  S  T  P  G  V  F  M  L  F  Y  E  Y  -

      TGACTTTGATGAAGAAACTGGGAAGATGAAGGATGATTTGGAAGCTATTCAGAGTAATAA
 8024 ------+---------+---------+---------+---------+---------+--- 8083
      ACTGAAACTACTTCTTTGACCCTTCTACTTCCTACTAAACCTTCGATAAGTCTCATTATT

b      D  F  D  E  E  T  G  K  M  K  D  D  L  E  A  I  Q  S  N  N  -

      TGAAGAAGATGATGAAAAAGAgCAGGAGCAAAAAGGAGTCCAGGAGCCAAAGGAAAGCCA
 8084 ------+---------+---------+---------+---------+---------+--- 8143
      ACTTCTTCTACTACTTTTTCTcGTCCTCGTTTTTCCTCAGGTCCTCGGTTTCCTTTCGGT

b      E  E  D  D  E  K  E  Q  E  Q  K  G  V  Q  E  P  K  E  S  Q  -

      AGAGCAAGGAGAAGGTGAAGAGCAAGAGGAAGGTCAAGAGCAGATGAAGTTCGAGAGAAC
 8144 ------+---------+---------+---------+---------+---------+--- 8203
      TCTCGTTCCTCTTCCACTTCTCGTTCTCCTTCCAGTTCTCGTCTACTTCAAGCTCTCTTG

b      E  Q  G  E  G  E  E  Q  E  E  G  Q  E  Q  M  K  F  E  R  T  -
```

FIGURE 19 (continued)

```
          AGAAGACCATAGAGATATTTCTGGTAAAGATGTAAACTAAGCTCGAGCACCACCACCACC
     8204 ------+---------+---------+---------+---------+---------+--- 8263
          TCTTCTGGTATCTCTATAAAGACCATTTCTACATTTGATTCGAGCTCGTGGTGGTGGTGG

b          E  D  H  R  D  I  S  G  K  D  V  N
ACCACTGAGATCCGGCTGCTAACAAAGCCCGAAAGGAAGCTGAGTTGGCTGCTGCCACCG
     8264 ------+---------+---------+---------+---------+---------+--- 8323
          TGGTGACTCTAGGCCGACGATTGTTTCGGGCTTTCCTTCGACTCAACCGACGACGGTGGC

b                              T7 Terminator Sequence
          CTGAGCAATAAC|TAGCATAACCCCTTGGGGCCTCTAAACGGGTCTTGAGGGGTTTTTTG|
     8324 ------+---------+---------+---------+---------+---------+-- 8382
          GACTCGTTATTGATCGTATTGGGGAACCCCGGAGATTTGCCCAGAACTCCCCAAAAAAC
```

1. Ub-human IL18, 3 hours
2. Ub-human IL18/Ubp-1, O hours
3. Ub-human IL18/Ubp-1, 3 hours
4. Ub-human IL18/Ubp-1, 18 hours C. Control- ProIL18/Casp 4

Western: Anti IL18

FIGURE 21

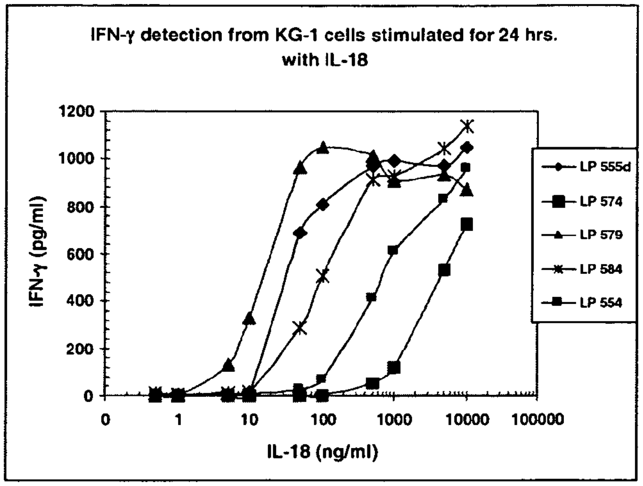

Description of different human/murine IL-18 samples (different lots/constructs)

| |
|---|
| **LP555d (standard)** E. COLI ICE-CLEAVED (*IN VITRO*) |
| LP 554 E. coli murine IL-18 Ice-cleaved (*IN VITRO*) |
| LP559 E. coli expressed mature IL-18 containing N-terminal methionine |
| LP574 E. coli expressed mature IL-18 containing N-terminal Methionine |
| LP579 Pichia expressed, secreted, mature IL18 |
| LP584 E.coli IL-18/ICE bicistronic co-expression (*IN VIVO*) |
| LP594 E. coli ICE-cleaved (*IN VITRO*) |
| LP613 E. coli caspase 4 cleaved (*IN VITRO*) |
| LP614 E. coli ICE co-expressed (*IN VITRO*) |
| LP623 caspase 4 co-expressed (*IN VIVO*) |

Figure 22

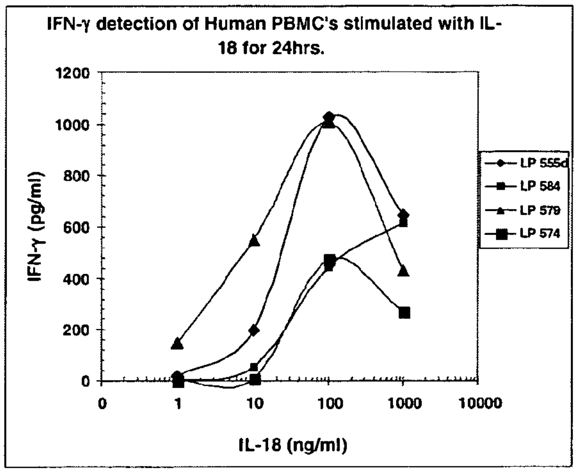

Description of different human/murine IL-18 samples (different lots/constructs)

| |
|---|
| **LP555d (standard)** E. COLI ICE-CLEAVED (*IN VITRO*) |
| LP 554 E. coli murine IL-18 Ice-cleaved (*IN VITRO*) |
| LP559 E. coli expressed mature IL-18 containing N-terminal methionine |
| LP574 E. coli expressed mature IL-18 containing N-terminal Methionine |
| LP579 Pichia expressed, secreted, mature IL18 |
| LP584 E.coli IL-18/ICE bicistronic co-expression (*IN VIVO*) |
| LP594 E. coli ICE-cleaved (*IN VITRO*) |
| LP613 E. coli caspase 4 cleaved (*IN VITRO*) |
| LP614 E. coli ICE co-expressed (*IN VITRO*) |
| LP623 caspase 4 co-expressed (*IN VIVO*) |

METHOD FOR PREPARING A PHYSIOLOGICALLY ACTIVE IL-18 POLYPEPTIDE

This is a 371 of International Application PCT/US01/18804, filed 11 Jun. 2001, which claims benefit from the following U.S. Provisional Applications: 60/211,832 filed 15 Jun. 2000; 60/224,128 filed 10 Aug. 2000; and 60/264,923, filed 30 Jan. 2001.

BACKGROUND OF THE INVENTION

The present invention relates to a process for producing a physiologically active polypeptide, more particularly, to a process for producing active human IL-18.

IL-18, also known as interferon-γ-inducing factor, is a recently discovered novel cytokine. Active IL-18 contains 157 amino acid residues. It has potent biological activities, including induction of interferon-γ-production by T cells and splenocytes, enhancement of the killing activity of NK cells and promotion of the differentiation of naïve $CD4^+$T cells into Th1 cells. In addition, human IL-18 augments the production of GM-CSF and decreases the production of IL-10. IL-18 has been shown to have greater interferon-γ inducing capabilities than IL-12 and signals through a different receptor and utilizes a distinct signal transduction pathway.

IL-18, the encoding nucleotide sequence, and certain physicochemical chemical properties of the purified protein is known (Ushio, S., et aL, 1996, J. Immunology, 156, 4274–4279; Dinarello, C. A., et al. 1998, J. Leukocyte Biology, 1998. 63, 658–664).

Kabushiki Kaisha Hayashibara Seibutsu Kayaku Kenkyujo's ("Hayashibara"), U.S. Pat. No. 5,192,324, which corresponds to EP 0692536, published on Jan. 17, 1996, discloses a mouse protein which induces IFN-gamma production by immunocompetent cells, the protein being further characterized as having certain physicochemical properties and a defined partial amino acid sequence. Also disclosed is a protein having a 157 aa sequence, two fragments thereof, DNA (471 bp) encoding the protein, hybridomas, protein purification methods, and methods for detecting the protein.

Hayashibara's U.S. Pat. No. 6,214,584, which corresponds to EP 0712931, published on May 22, 1996, discloses a 157 aa human protein and homologues thereof, DNA encoding the protein, transformants, processes for preparing the protein, monoclonal antibodies against the protein, hybridomas, protein purification methods, methods for detecting the protein, and methods of treatment and/or prevention of malignant tumors, viral diseases, bacterial infectious diseases, and immune diseases.

Incyte Pharmaceuticals, Inc.'s, WO 97/24441, published on Jul. 10, 1997, discloses a 193 amino acid protein corresponding to IL-18 precursor and encoding DNA.

In human cells, polypeptides formed by the expression of genes may be processed by intracellular enzymes to be partially digested and to receive sugar chains. Polypeptides to be satisfactorily incorporated into pharmaceuticals may be those which were processed similarly as in human cells. It is known that most cytokines are usually produced as precursors with no biological activity, and then processed by intracellular enzymes to be converted into active polypeptides.

The IL-18 polypeptide usually exists in human cells in the form of a precursor of 193 amino acids and no biological activity. The precursor IL-18 is also referred to as Pro-IL-18. One method of producing active IL-18 from its precursor is taught by Hayashibara's U.S. Pat. No. 5,879,942, which corresponds to EP 0819757, published on Jan. 21, 1998. The patent discloses an enzyme or a protein which converts a precursor of IL-18 into active IL-18.

Another method of producing active IL-18 from its precursor is taught by Hayashibara's U.S. Pat. No. 5,891,663, which corresponds to EP 0821005, published on Jan. 28, 1998. The patent discloses contacting precursor IL-18 with interleukin-1β-converting enzyme ("ICE"). The teachings of the patents and references are incorporated by reference.

The role of ICE as a mediator of apoptosis and inflammation has been extensively studied in the literature. It is also known that ICE can process precursors of both Interleukin-1 and Interleukin-18 to active forms (Thomberry, N A, et al., 1992, Nature 356, 768–774; Gbayur, T et al., 1997, Nature 386, 619–623).

SUMMARY OF THE INVENTION

The present invention provides methods for the in vitro activation of precursor of human IL-18 (also known as Pro-IL-18) with an activating enzyme comprising, contacting the precursor human IL-18 with an activating enzyme, such as caspase 4 or caspase 5. More specifically, the present invention provides a method by which caspase 4 and caspase 5 act on a precursor of IL-18 to cleave a specific site to produce an active polypeptide that induces IFN-γ production in immunocompetent cells.

The present invention further provides methods for the in vivo activation of precursor of human IL-18 comprising co-expressing the protein with an activating protease. More specifically, the present invention provides methods for the in vivo activation of IL-18 using proteasese such as, caspase 4, also known as $ICE_{REL}$II, caspase 5, also known as $ICE_{REL}$III, and ubiquitin-specific protease, which act on a precursor of the IL-18 polypeptide to convert it into an active polypeptide that induces IFN-γ production.

BRIEF DESCRIPTION OF TIRE ACCOMPANYING DRAWINGS

FIG. 1 shows the amino acid sequence of human precursor IL-18 (SEQ ID NO:1)

FIG. 2 shows the nucleic acid sequence encoding full-length human IL-18 (SEQ ID NO:2).

FIG. 3 shows the amino acid sequence of active human IL-18 (SEQ ID NO:3).

FIG. 4 shows the amino acid sequence of the 6-his tagged N-terminally truncated caspase 4 (SEQ ID NO:4).

FIG. 5 shows the nucleic acid sequence encoding the amino acid sequence of the 6-his tagged N-terminally truncated caspase 4 (SEQ ID NO:5).

FIG. 6 shows the amino acid sequence of the 6-his tagged N-terminally truncated caspase 5 (SEQ ID NO:6).

FIG. 7 shows the nucleic acid sequence encoding the amino acid sequence of the 6-his tagged N-terminally truncated caspase 5 (SEQ ID NO:7).

FIG. 9 shows a sequence of Pro-IL-18/Caspase 4 expression cassette within pET28 (SEQ ID NO:8).

FIG. 10 shows the annotated sequence of Pro-IL-18/Caspase 4 expression cassette. Numbering corresponds to the position within the pET28a vector.

FIG. 13 shows a sequence of Pro-IL-18/Caspase 5 expression cassette within pET28 (SEQ ID NO:9).

FIG. 14 shows the annotated sequence diagram of Pro-IL-18/truncated caspase-5 expression cassette detailing regulatory sequence features and translation of Pro-IL-18 and truncated caspase-5. Numbering corresponds to the positioning within the pET28a vector

FIG. 16 shows the amino acid sequence of Ub-IL-18 (SEQ ID NO: 10).

FIG. 17 shows the nucleic acid sequence encoding the amino acid sequence of Ub-IL-18 (SEQ ID NO:11).

FIG. 18 shows the nucleic acid sequence of Ub-IL-18/Ubp-1 expression cassette within the pET28 vector (SEQ ID NO:12).

FIG. 19 shows the annotated sequence of Ub-IL-18/Ubp-1 within the pET28 vector. Numbering corresponds to the position within pET28.

FIG. 21 shows IL-18 activity assay using KG-1 (human myelomonocytic cell line) cells and to monitor IFN-γ production (IL-18 expressed in various ways as indicated).

FIG. 22 shows IL-18 activity assay using purified human PBMCs to monitor IFN-γ production (IL-18 expressed in various ways as indicated).

DETAILED DESCRIPTION OF THE INVENTION

Figure 8:
FIG. 8 is a schematic diagram of a bicistronic expression cassette contained within pET28-ProIL-18/Casp 4 for co-expressing of Pro-IL-18 and truncated caspase 4 in *E. coli.*

Caspase 4 and 5 are members of a family of cysteine proteases that include Interleukin-1β converting enzyme (ICE), which preferentially cleave substrates containing a protease activation motif comprising the amino acid sequences XEYD, wherein X is selected from a group of amino acids consisting of W, L, F, Y, I, V, D, or E ; E is glutamic acid; Y is selected from a group of amino acids consisting of H, I, A, T, S, P or E; and D is aspartic acid (Munday, N. A., et al., 1995, J. Biol. Chemistry, 270, 15870–15876; Talanian, R. V. et al, 1997, J. Biol. Chemistry 272, 9677–82; Thomberry, N. A. et al. 1997 J. Biol. Chemistry 272, 17907–11). The substrate recognition of caspase-5 is thought to be essentially the same for ICE and caspase-4 and distinct from other members of the caspase (Talanian, R. V. et al, 1997, J. Biol. Chemistry 272, 9677–82; Thomberry, N. A. et al. 1997 J. Biol. Chemistry 272, 17907–11). Caspase 4 is disclosed in EP-B-0 754 234. Caspase 5 is disclosed in U.S. Pat. No. 5,552,536 and U.S. Pat. No. 5,760,180.

Ubiquitin-specific proteases are a family of ATP-independent enzymes that can precisely cleave the evolutionarily conserved 76 amino acid ubiquitin peptide from the N-terminus of proteins that are fused to it. These proteases specifically cleave the peptide bond between the carboxyl-terminal amino acid residue of a ubiquitin protein and the α-amino group of any non-ubiquitin protein to which ubiquitin is joined. Ubiquitin-specific proteases from Saccharomyces cerevisiae, Ubp1, Ubp-2, and Ubp-3, for example, are known and can be recombinantly expressed to catalyze deubiquitination reactions that target ubiquitin fusion proteins both in vivo and in vitro (Baker, R T et al., 1992, J. Biol. Chem. 267: 23364–23375; Baker, R T et al., 1994 J. Biol. Chem. 269: 25381–25386). The specificity of Saccharomyces cerevisiae ubiquitin-specific proteases allows for the precise removal of ubiquitin from any peptide with the exception of those that start with proline. Ubiquitin-specific protease from other species such as mouse Unp and its human homologue Unph, are capable of efficient cleavage even in front of proline (Gilchrist C A et al. 1997, J. Biol. Chem. 272:32280–32285. Thus, virtually any desired N-terminus can be generated through the removal of a precisely fused ubiquitin peptide when combined in vitro or co-expressed with ubiquitin-specific proteases. Ubiquitin specific proteases are disclosed in U.S. Pat. Nos. 5,212,058; 5,683,904; 5,391,490; and 5,494,818.

Any natural and artificially produced caspase 4, caspase 5, or ubiquitin protease can be used in the present invention as long as they produce active polypeptides that induce IFN-γ production in immunocompetent cells independently of their structures, sources and origins.

In human cells, polypeptides formed by the expression of genes may be processed by intracellular enzymes. Intracellular enzymes cleave the precursor proteins, such as Pro-IL-18, into their active form. Polypeptides to be satisfactorily incorporated into pharmaceuticals should receive processing similar to the processing polypeptides receive in human cells. The polypeptides usually exist in human cells in the form of a precursor and no biological activity. It is known that most cytokines, including the IL-18 polypeptide, are usually produced as precursors with no biological activity, and then processed by intracellular enzymes to be converted into active polypeptides.

The precursor of IL-18 as referred to in the present invention exists, for example, in cells which inherently produce the polypeptide, in mammalian host cells, and in a bacterial system, such as *E. coli,* transformed by introducing a DNA, e.g., a DNA with the nucleotide sequence of SEQ ID NO:2, containing a region which encodes the polypeptide. Using such mammalian and bacterial host cells, precursor IL-18 can be co-expressed with proteases to generate active IL-18.

In Vitro Cleavage

The present invention provides methods for the in vitro activation of a precursor polypeptide, such as the precursor of IL-18 comprising, contacting the precursor polypeptide with an activating enzyme.

In a preferred embodiment, the present invention provides a method for the in vitro activation of precursor of human IL-18 comprising, contacting the precursor human IL-18 with caspase 4 or caspase 5.

In a preferred embodiment, the precursor of IL-18 is activated in vitro by cleaving with the activating enzyme which recognizes a specific protease activation motif comprising the amino acid sequence ATYD, wherein X is selected from a group of amino acids consisting of W, L, F, Y, I, V, D or E; and Y is selected from a group of amino acids consisting of of H, I, A, T, S, P or E.

In a further preferred embodiment, the precursor of IL-18 is activated in vitro by cleaving the peptide linkage between the aspartic acid 36 and tyrosine 37 in SEQ ID NO:1 with caspase 4 or caspase 5 to produce an active polypeptide that induces IFN-γ production in immunocompetent cells.

Generally, caspase 4 or caspase 5 can be obtained from cells, which inherently produce it, and transformants obtained by applying recombinant DNA technology. Examples of such cells are those which were established from mammal and human cells such as epithelial cells, endothelial cells, interstitial cells, cartilage cells, monocytes, granulocytes, lymphocytes, and established cell lines thereof. Examples of the transfonnants include transformed microorganisms and animal cells obtained by introducing a DNA encoding caspase 5 into microorganisms and animal cells. Caspase 4 or caspase 5 is prepared by culturing these transformants in conventional culture media used in this field, either treating them with ultrasonics in the form of intact cultures or after separated from the cultures or soaking the transformants in hypotonic solvents, applying to the resulting cell debris or mixtures containing culture supernatants and cell debris the following conventional techniques used for purifying enzymes in this field; salting out, dialysis, filtration, concentration, separatory sedimentation, ion-exchange chromatography, gel filtration chromatography, adsorption chromatography, isoelectric chromatography, hydrophobic chromatography, reverse-phase chromatography, affinity chromatography gel electrophoresis and electrofocusing. Two or more of these purification methods can be used in combination. The DNA encoding caspase 4 (FIG. 5) (SEQ ID NO:5) and caspase 5 (FIG. 7) (SEQ ID NO:7) and transformants which produce caspase 4 and caspase 5 are known in the art. For example, the enzymes may be produced in active form in *E. coli* by expression of N-terminally truncated peptides lacking the pro region, as described (Munday N A et al., 1996, J. Biol. Chem 26:15870–76.)

Cells which produce the precursor polypeptide, such as Pro-IL-18, inherently or those which were transformed to produce the precursor are cultured in nutrient culture media. Preferred culture media include culture media well known in the art, such as Luria-Bertani medium or other rich medium for culturing *E. coli* comprising tryptone and yeast extract.

Caspase 4 or caspase 5, obtained using the above method, is allowed to coexist in the resulting cultures or added to the resulting mixtures or cell debris after disrupting the proliferated cells separated or unseparated from the cultures. The amount of caspase 4 or caspase 5 required is less than the equimolar of the precursor. The caspase 4 or caspase 5 is contacted with the precursor at temperatures and pHs, which allow the caspase 4 or caspase 5 to act on the precursor, usually, the caspase 4 or caspase 5 is allowed to react with the precursor until the desired amount of active polypeptide is formed from the material precursor at temperatures of about 4°–40° C. and pHs of about 6–9. The preferred temperature is about 25° C. and the preferred pH is about 7.2. Thus, reaction mixtures containing the active polypeptide can be obtained.

The activity of caspase 4 or caspase 5 may be assayed and expressed by units for activity according to the μg processed polypeptide produced per jig caspase 4 or caspase-5 per minute.

In Vivo Co-Expression

The present invention further provides methods for the in vivo activation of a precursor polypeptide, such as a precursor of IL-18 comprising co-expressing the protein with an activating protease. More specifically, the present invention provides methods for the in vivo activation of IL-18 comprising the bicistronic co-expression of polypetides, such as IL-18, with proteasese such as, caspase 4, also known as $ICE_{REL}$II, caspase 5, also known as $ICE_{REL}$III, and ubiquitin.

In a preferred embodiment, human caspase 4, also known as $ICE_{REL}$II, is co-expressed bicistronically with human Pro-IL-18 to allow for the in vivo processing of Pro-IL-18 into active IL-18.

In another preferred embodiment, truncated human caspase 4 (SEQ ID NO. 4), is co-expressed bicistronically with human Pro-IL-18 to allow for the in vivo processing of Pro-IL-18 (SEQ ID NO:1) into active IL-18 (SEQ ID NO:3).

In another preferred embodiment, human caspase 5, also known as $ICE_{REL}$III, is co-expressed bicistronically with human Pro-IL-18 to allow for the in vivo processing of Pro-IL-18 into active IL-18 (SEQ ID NO:3).

In yet another preferred embodiment, ubiquitin protease 1 (Ubp-1) is co-expressed bicistronically with Ubiquitin-IL-18 (Ubp-IL-18) for the in vivo processing of Ub-IL-18 into active IL-18.

In yet another preferred embodiment, ubiquitin protease 1 (Ubp-1) is co-expressed bicistronically with Ubiquitin-IL-18 (Ubp-IL-18) for the in vivo processing of UB-IL-18 (SEQ ID NO:9) into active IL-18 (SEQ ID NO.3).

In the most preferred embodiment, truncated human caspase 5 (SEQ ID NO. 5), is co-expressed bicistronically with human Pro-IL-18 to allow for the in vivo processing of Pro-IL-18 (SEQ ID NO: 1) into active IL-18 (SEQ ID NO:3).

Figure 11:
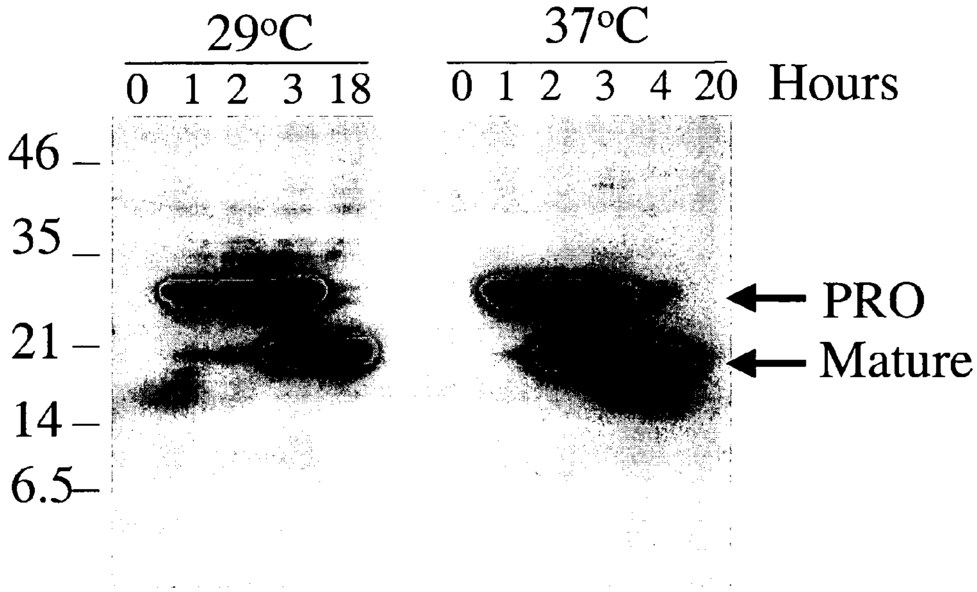
FIG. 11 shows Pro-IL-18/Caspase 4 induction.
Figure 12:
FIG. 12 is a Schematic diagram of bicistronic expression cassette contained within pET28-Pro-IL18/truncated caspase-5 for co-expression of Pro-IL8 and Caspase-5 in *E. coli.*
Figure 15:
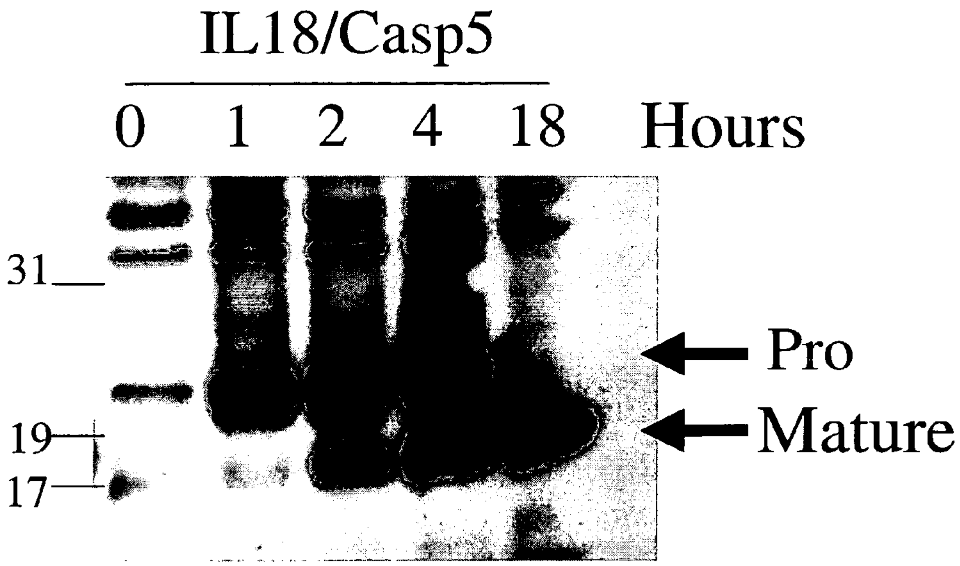
FIG. 15 shows Pro-IL-18/Caspase 5 induction.

A DNA encoding caspase 4 or caspase 5 and a DNA encoding a precursor of the polypeptide are both introduced into an appropriate bacterial or mammalian host cell to transform it. In this case, caspase 4 or caspase 5, formed by the DNA expression, acts on a precursor of the polypeptide, formed by the DNA expression in the same transformant, to form an active polypeptide (FIGS. 11 and 15). Preferred host cells are epidermal-, interstitial-, neuroblast-, hematopoietic-cell lines, which are derived from humans, monkeys, mice and hamsters and used conventionally as hosts, such as 3T3 cells including 3T3-Swiss albino cells (ATCC CCL 92), C1271 cells (ATCC CRL 1616), CHO cells including CHO-K1 cells (ATCC CCL 61), CV-1 cells (ATCC CCL 70), COS cells including COS-1 cells (ATCC CCL 1650), HeLa cells (ATCC CCL 2), MOP cells including MOP-8 cells (ATCC CRL 1709) and mutants thereof. Most preferred host cells are *E. coli.* The most preferred method is of introducing DNA encoding caspase 4 or 5 and a DNA encoding a precursor of the polypeptide into *E. coli* is chemical transformation with rubidium chloride, which is well known in the art. Methods to introduce a DNA encoding caspase 4 or caspase 5 and a DNA encoding a precursor of the polypeptide into mammalian host cells include conventional DEAE-dextran method, phosphoric acid-calcium method, electroporation, lipofection, microinjection, and virus-infection method using retrovirus, Adenovirus, herpesvirus and vaccinia virus. In this case, vectors such as pCD, pcDL-SRα, pKY4, pCDM8, pCEV4, pME18 S and pSV2-gpt, including appropriate promoters, enhancers, replication origins, termination sites, splicing sequences, polyadenylation sequences and/or selection markers can be used following standard techniques described in Ausubel F M et al., 1994 Current Protocols in Molecular Biology, New York: Greene Publishing Assoc. and Wiley Interscience. Clones, which were observed by immunological detection to produce an activated polypeptide, were selected by choosing the desired clone from transformants after culturing in nutrient culture media. Cultures containing the active polypeptide can be obtained by culturing the cloned transformant with conventional nutrient culture used in this field. As for cells which inherently produce a precursor of the polypeptide and other cells which were transformed to produce the polypeptide, they may produce the precursor along with activating enzymes, which activate the polypeptide, such as caspase 4, caspase 5, and ubiquitin. Recombinant DNA technologies using mammalian host cells are disclosed in detail in Glutzman, Cell, 23:175 (1981) Mullingan, PNAS78:2072 (1981). Recombinant DNA technologies using bacterial host cells are described in Protein Expression:A Practical Approach, S. J. Higgins and B. D. Hames eds. 1999, New York, Oxford University Press.

While the resulting reaction mixtures and cultures containing an active IL-18 polypeptide can be used intact as an IFN-γ inducer, in a preferred embodiment, cells in the cultures are disrupted by ultrasonics, cell lysis enzymes and/or surfactants, followed by separating the polypeptide from the resulting cells and cell debris by filtration, centrifugation, etc., following standard industry procedures described in Protein Purification:Principles and Practice, Cantor, C. R. ed. 1993, New York, Spinger-Verlag. The polypeptide free of cells and cell debris may be purified by conventional purification methods used to purify biologically active substances in this field, for example, salting out, dialysis, filtration, concentration, separatory sedimentation, ion-exchange chromatography, gel filtration chromatography, adsorption chromatography, isoelectric chromatography, hydrophobic chromatography, reverse-phase chromatography, affinity chromatography, gel electrophoresis and electrofocusing. If necessary, two or more of these purification methods can be used in combination. The resulting purified polypeptide can be concentrated and lyophilized into a liquid or solid product to meet their final uses.

The bicistronic expression cassettes of the present invention are versatile vectors which can be used for the in vivo processing of virtually any peptide containing the appropriate caspase 4/caspase 5 or ubiquitinase cleavage recognition sites as have been previously described (Tobias, J. W. et al., *Journal of Biological Chemistry,* 1991. 266(18): p.12021.12028; Talanian, R. V. et al., *Journal of Biological Chemisty,* 1997. 272(15): p.9677–9682). Bicistronic expression offers advantages over other co-expression strategies because both genes are tied to the same transcription unit, ensuring consistent expression of both genes over time. This is in contrast to dual plasmid systems where one plasmid can be lost over time, or single plasmid dual promoter systems where expression may vary from each promoter from one experiment to the next. In particular, the bicistronic expression systems described here are ideally suited for the in vivo activation of enzymes, cytokines, growth factors, and other proteolytically activatable proteins, thereby enabling large-scale production of such proteins from cells in a single step and eliminating the need for a separate in vitro activation step.

Activating proteases, caspase 4 (Ala105 to Asn377) or caspase 5 (Ile146 to Asn418), were subcloned as N-terminal 6-His fusions immediately following the Pro-IL-18 sequence in order to generate a transcriptional fusion of the two genes. A T7 terminator sequence is located downstream of the caspase-4 sequence for translational termination of the bicistronic transcription unit. A small intergenic region including a defective Shine-Dalgamo sequence was also added to permit only minimal translation initiation from the caspase-4 sequence (FIGS. 10, and 14). Other regulatory regions include a 25 basepair lac operator sequence located immediately downstream of the 17 basepair promoter region which is bound by lac repressor encoded by a copy of the lac-I gene located on the plasmid, thereby suppressing basal transcription in the absence of T7 RNA polymerase. The resultant plasmids designated ProIL18/Casp4 and ProIL18/Casp5 were then separately transfected into *E. coli* BL21 (DE3) strain that contains an inducible chromosomal copy of the T7 polymerase gene.

The transcription of the bicistronic cassette is under the direction of the T7 promoter, which is controlled by the phage T7 RNA polymerase protein, encoded from a lysogenic copy of the T7 RNA polymerase gene. This chromosomal copy of T7 polymerase is itself under lacUV5 promoter control, inducible by the addition of isopropyl-1-thio-b-D-galactopyranoside. Induction leads to the coordinate transcription and translation of Pro-IL-18 and His-caspase-4 or His-caspase-5. Nascently translated caspase-4 or caspase-5 is autoprocessed to an active species, which initiates the proteolytic activation ProIL-18. Both the translated precursor IL-18 as well as the post-translationally activated IL-18 are mainly soluble inside *E. coli.* Mature active IL-18 containing an N-terminal tyrosine is purified directly from bacterial cell lysates following induction by conventional chromatography methods. Cleavage to mature IL-18 with caspase-4 is complete by 4 hours at 37° C. or by 18 hours at 29° C. (FIG. 11) and cleavage to mature IL-18 with caspase-5 is complete by 18 hours at 29° C. (FIG. 15).

In the most preferred embodiment, the present invention uses a truncated caspase 4, as shown in FIG. 4 (SEQ ID NO:4 and SEQ ID NO:5), or truncated caspase 5 as shown in FIG. 5 (SEQ ID NO: 6 and SEQ ID NO: 7). Truncation of caspase 4 and caspase 5 is disclosed in Munday, N. A., et al., 1995, J. Biol. Chemistry, 270, 15870–15876.

Figure 20:
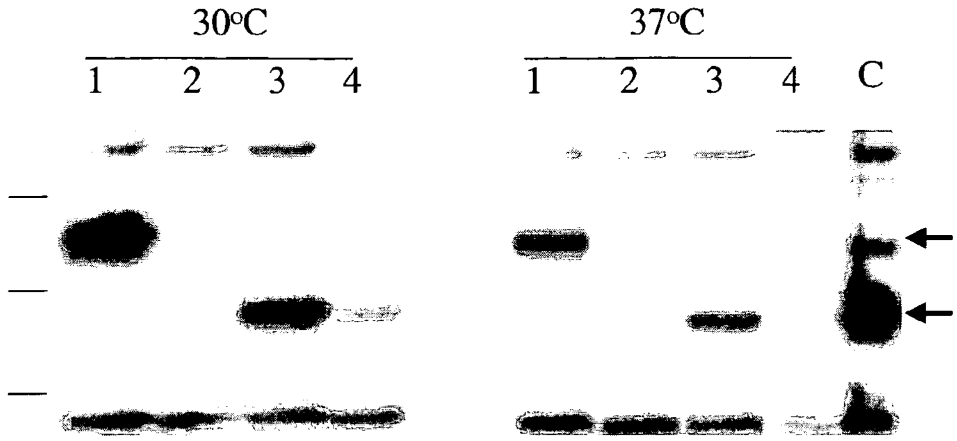
FIG. 20 shows Ub-IL-18 expression and processing by Ubp-1.

The present invention further provides a method for creating an active polypeptide by co-expression of a ubiquitin-specific protease with an N-terminal ubiquitin IL-18 fusion (precursor) which is converted to active IL-18 by the ubiquitin c-terminal hydrolase activity. A 76 amino acid ubiquitin protein containing an authentic N-terminal tyrosine is fused to the mature N-terminus of human IL-18 and coexpressed with a ubiquitin-specific protease in *E. coli* for example as shown in SEQ ID NO:10 and SEQ ID NO:11. Ubiquitin is a highly conserved 76-residue protein found in eucaryotic cells that function to mark proteins for degradation (Baker, R. T., Current Opinion in Biotechnology, 1996. 7(5): p. 541–6). Ubiquitin is specifically cleaved from proteins by the action of ubiquitin-specific proteases that are endogenously expressed in eucaryotic cells but which are absent in bacteria. The co-expression of ubiquitin fused proteins with ubiquitin-specific proteaese in *E. coli* also leads to the efficient removal of ubiquitin (Baker, R. T. et al., Journal of Biological Chemistry, 1992. 267(32): p. 23364–75) (FIG. 20). In addition, most of these deubiquitinating enzymes are capable of cleaving in front of virtually any amino acid with the exception of proline. Thus, cleavage of ubiquitin from mature IL-18 is possible despite the presence of the large aromatic tyrosine residue in the P1' position.

The co-expression of Ubiquitin-IL-18 (Ub-IL-18) and Ubiquitin protease-1(Ubp-1) (Tobias, J. W. et al., *Journal of Biological Chemistry,* 1991. 266(18): p.12021.12028) is accomplished through the bicistronic expression of the two genes under inducible T7 promoter control. Mature IL-18 is expressed as an N-terminal fusion with the evolutionarily conserved 76 amino acid ubiquitin peptide. The Ub-IL-18 cDNA is subcloned under the control of the T7 RNA polymerase promoter within pET28a vector. Subsequently, the cDNA encoding full-length ubiquitin-specific protease is subcloned downstream preceding the T7 terminator sequence (FIG. 19). Both Ub-IL-18 and Ubiquitin-specific protease cDNA's are transcribed into a single mRNA transcript from which Ub-IL-18 and Ubiquitin-specific protease proteins are separately translated.

As described above, the active human IL-18 polypeptide, obtained by the present methods has an activity of inducing the production of IFN-γ as a useful biologically active substance, stimilates the production of IFNg from KG-1 (human myelomonocytic cell line) cells FIG. 21 and purified human PBMCs (FIG. 22).

All publications and patents are hereby incorporated by reference. The following examples further explain but do not limit the present invention:

EXAMPLE 1

Preparation of Precursor IL-18 (pro-IL-18)

Human-precursor IL-18 was expressed as an N-terminal hexa-histidine tagged fusion in *E. coli*. The expression plasmid, ProEx-IL18, was derived from a vector, pPROBX-1 (Life Technologies) containing the Trc promoter and Iaclq for inducible expression with isopropyl-1-thio-β-D-galactopyranoside (IPTG). In order to construct the recombinant expression vector, a DNA fragment containing the entire caspase 5 precursor gene was PCR amplified from a cDNA clone, tailing 5' with Nde I and 3' with Bam HI restriction endonuclease sites. The amplified product was subcloned between these two restriction sites in pPROEX-, thus generating an in frame N-terminal fusion with the hexa-histidine coding sequence present in the vector.

The resultant plasmid was expressed in DH10B host cells following induction with 1 mM IPTG for 5 hours at 37° C. Recombinant protein was harvested from cell pellets obtained following centrifugation of the induced cultures.

EXAMPLE 2

Purification of pro-IL-18

1.5 kg of *E coli* cells expressing pro-IL-18 as described in EXAMPLE 1 was suspended in 3.6 L lysis Buffer C (50 mM Tris HCl, 10 mM BME, 0.5 M NaCl, 5% glycerol, 1 ug/ml pepstatin A, 1 ug/ml leupepsin, 0.4 mM AEBSF), lysed by two passes through Microfluidics at 12,000 psi, centrifuged at 28,000 xg, and 3.7 L supernatant were collected. 600 ml of NiNTA agarose preequilibrated with Buffer C containing 5 mM imidazole (Buffer D) was added to the supernatant and incubated the slurry for one hour to capture pro-IL-18. The slurry was centrifuged at low speed (3,000 rpm), the supernatant was decanted, and the slurry was packed in a column. The column was washed with Buffer D and pro-IL-18 was eluted with 300 mM imidazole in Buffer C. The pool was dialyzed in Buffer E (25 mM HEPES, 10 mM BME, pH 8.0) and applied to DEAE ToyoPearl 650M column equilibrated with the same buffer. The column was eluted with a linear gradient of 0 to 0.5 M NaCl in Buffer E. The pool contained 650 mg of >90% pure pro-IL-18.

EXAMPLE 3

Preparation of Caspase 4

Human caspase-4 was also expressed as an N-terminal Hexa-histindine tagged fusion in *E. coli*. The expression plasmid, pET16b-caspase 4, was derived from a vector pET16b (Novagen) containing the phage T7 promoter. The recombinant vector was constructed by PCR amplification of the caspase-4 active domain (amino acids Ile146 to Asn418) incorporating a hexa-histidine coding sequence at the N-terminus and tailing with Nco I and Xho I restriction endonuclease sites. The resultant PCR product was then subcloned between these two restriction sites to generate the N-terminal Hexa Histidine-Caspase 4 fusion vector.

The resultant plasmid was transformed into the lysogenic BL21 DE3 *E. coli* strain containing a chromosomal copy of T7 RNA polymerase under lacUV5 promoter control enabling inducible expression of caspase 4 following induction with 1 mm IPTG. Active protein was purified from cell pellets isolated following induction at 37° C. for 3 hours.

EXAMPLE 4

Purification of Caspase 4

When *E. coli* cells expressing N-terminal hexa-His tagged human caspase 4 described in Example 2 are lysed, caspase 4 activity can be detected in the lysate supernatant. When the protein is captured on NiNTA agarose beads from the supernatant, both p10 and p20 are recovered. This indicates that caspase 4 protease domain is activated during cell culture through autocleavage at the junction of p10 and p20 and remains as a soluble noncovalent heterodimer. With this information, hexa-His tagged p20/p10 heterodimer can be purified. The entire process is carried out at 4° C. to avoid any further breakdown of the molecule.

Approximately 400 g of wet *E. coli* cell pellet was suspended in 1.6 L of lysis buffer containing 25 mM HEPES, 0.1% CHAPS, 500 mM NaCl, 10 mM beta mercaptoethanol (BME) at pH 7.4, and 10% glycerol (Buffer A) and lysed by two passes through Microfluidics at 12,000 psi. The lysate was centrifuged at 30,000xg for one hour and lysate supernatant, 1.7 L, was recovered. NiNTA agarose, 150 ml, which was preequilibrated with lysis buffer containing 5 mM imidazole, was added to the lysate supernatant, the suspension was adjusted to pH 8.0 with 2 N NaOH, and caspase 4 was batch-absorbed for one hour. NiNTA agarose was packed in the column, washed with 5 mM and 25 mM imidazole in Buffer A sequentially to remove impurities, and caspase 5 was eluted with 300 mM imidazole in Buffer A. The protein was dialyzed against Buffer B (25 mM HIEPES, 0.1% CHAPS, 10% glycerol, 10 mM BME, pH 8.0) and applied to DEAE ToyoPearl 650M column preequilibrated with the same buffer. Caspase 4 was eluted from the column with 100 mM NaCl in the same buffer. Fractions displaying highest specific activity of caspase 4 using fluorescent peptide substrate, LEED-AMC, were pooled.

EXAMPLE 5

In vitro Activation and Preparation of Polypeptide

Pro-IL-18 purified as described in Example 2 was incubated with Caspase 4 at 1:500 w/w ratio for 3 hours at room temperature. The cleavage reaction of prodomain was completed >90% according to SDS-PAGE analysis. To the reaction mixture, 140 ml of NINTA agarose in Buffer D was added, incubated for one hour, and poured to sintered glass funnel to recover unbound material containing mainly mature IL-18. Small amounts of remaining pro-IL-18, prodomain, caspase 4, and other impurities were bound to NINTA agarose. The unbound solution was adjusted to 25 mM DTT, incubated for one hour to complete reduction reaction, adjusted the pH of the solution to 6.0 by adding 2 M phosphoric acid, and concentrated to 86 ml using YM10 membrane. The concentrated sample was applied to Superdex 75 column equilibrated with 10 mM NaPhosphate pH 6.0 containing 0.1 M NaCl. Pooled fractions contained 560 mg of mature IL-18.

EXAMPLE 6

In vivo Activation and Preparation of Polypeptide

Activation of IL-18 can also be achieved in vivo through the simultaneous expression of human precursor IL-18 and caspase-4. Pro-IL-18 is co-expressed bicistronically in *E. coli* from a single transcript with human caspase-4 within the expression plasmid, pET28-Pro-IL-18/Casp4 FIG. 8). The human pro-IL-18 gene is subcloned into pET28a (Novagen) under the control of the T7 promoter including an efficient Shine-Dalgarno sequence for optimal translation initiation from the Pro-IL-18 sequence (FIG. 8). The caspase 4 gene (Ile146 to Asn418) was subcloned immediately after the Pro-IL-18 sequence including a defective Shine-Dalgarno sequence, permitting minimal translation initiation from the caspase 4 sequence. A T7 terminator sequence was included for translational termination following the bicistronic transcription unit. The resultant construct was then transfected into a BL21 (DE3) host containing an inducible chromosomal copy of the T7 polymerase gene. Induction of this construct in this host with 1 mM IPTG resulted in the coordinate transcription and translation of pro-IL-18 and pro-caspase 4. Nascently translated pro-caspase 4 is autoprocessed to an active species which initiates the proteolytic activationof pro-IL-18. FIG. 11 shows a time course of IL-18 activation over 18 hours at 29° C. following 1 mM IPTG induction (0–18 hours).

EXAMPLE 7

In vivo Activation of Caspase 4

The in vivo activation of Caspase-4 is described in (Munday, N. A., et al., 1995, J. Biol. Chemistry, 270, 15870–15876). Expression of a truncated form of caspase-4 beginning at Ala 59, lacking the proregion in *E. coli,* leads to self-activation by cleavage into P10 and P20 subunits which assemble into an active enzyme heterodimer. The delay in caspase-4 activation is translated into a delay in the cleavage and activation of Pro-IL-18 to mature IL-18 (FIG. 9). This enables accumulation of the more stable Pro-IL-18 prior to its cleavage to mature IL-18 which is less stable in cells.

EXAMPLE 8

Purification of Human IL-18 Coexpressed with Caspase 4

66 g of *E. coli* cells expressing IL-18 as described in Example 6 were suspended in 130 ml of 0.1 M HEPES pH 7.5 containing 1 mM EDTA and 10 mM DTT (entire process was performed at 4° C. and in the presence of 10 mM DTT except the last step to maintain free SH) and lysed at 15,000 psi by two passes using Microfluidics. The lysate (230 ml) was centrifuged at 34,000 xg for 30 min. The supernatant (200 ml) was diluted to 1 L with 25 mM HEPES pH 7.0 and flowed through two columns in tandem, ToyoPearl SP 650M and ToyoPearl DEAE 650M. Much of the impurities derived from *E. coli* cells were bound to the columns. The flow-through material was adjusted to pH 9.5 with 25 mM bistris propane, diluted to 2 L and applied to Source 15Q column equilibrated with 25 mM bistris propane HCl pH 9.5. The column was eluted with a linear gradient of 0 to 0.5 M NaCl in the same buffer. Fractions containing IL-18 were identified using Vydac C4 RP-BPLC and pooled (250 ml). The pool was concentrated to 50 ml using YM10 membrane and applied to Superdex 75 column which was preequilibrated with 10 mM NaPO4 pH 6.0 containing 1 mM EDTA and 0.15 M NaCl (no DTT for in vivo use).

EXAMPLE 9

Preparation of Truncated Caspase 5

Human truncated caspase 5 was also expressed as an N-terminal Hexa-histindine tagged fusion in *E. coli.* The expression plasmid, pET16b- truncated caspase 5, was derived from a vector pET16b (Novagen) containing the phage T7 promoter. The recombinant vector was constructed by PCR amplification of the truncated caspase 5 active domain (amino acids Ile146 to Asn418) incorporating a hexa-histidine coding sequence at the N-terminus and tailing with Nco I and Xho I restriction endonuclease sites. The resultant PCR product was then subcloned between these two restriction sites to generate the N-terminal Hexa Histidine- truncated caspase 5 fusion vector.

The resultant plasmid was transformed into the lysogenic BL21 DE3 *E. coli* strain containing a chromosomal copy of T7 RNA polymerase under lacUV5 promoter control enabling inducible expression of truncated caspase 5 following induction with 1 mM IPTG. Active protein was purified from cell pellets isolated following induction at 37° C. for 3 hours.

EXAMPLE 10

Purification of Truncated Caspase 5

When *E. coli* cells expressing N-terminal hexa-His tagged human truncated caspase 5 described in EXAMPLE 9 are lysed, truncated caspase 5 activity can be detected in the lysate supernatant. When the protein is captured on NiNTA agarose beads from the supernatant, both p10 and p20 are recovered. This indicates that truncated caspase 5 protease domain is activated during cell culture through autocleavage at the junction of p10 and p20 and remains as a soluble noncovalent heterodimer. With this information, hexa-His tagged p20/p10 heterodimer can be purified. The entire process is carried out at 4° C. to avoid any further breakdown of the molecule.

Approximately 400 g of wet *E. coli* cell pellet was suspended in 1.6 L of lysis buffer containing 25 mM HEPES, 0.1% CHAPS, 500 mM NaCl, 10 mM beta mercaptoethanol (BME) at pH 7.4, and 10% glycerol (Buffer A) and lysed by two passes through Microfluidics at 12,000 psi. The lysate was centrifuged at 30,000xg for one hour and lysate supernatant, 1.7 L, was recovered. NINTA agarose, 150 ml, which was preequilibrated with lysis buffer containing 5 mM imidazole, was added to the lysate supernatant, the suspension was adjusted to pH 8.0 with 2 N NaOH, and caspase 5 was batch-absorbed for one hour. NiNTA agarose was packed in the column, washed with 5 mM and 25 mM imidazole in Buffer A sequentially to remove impurities, and caspase 5 was eluted with 300 mM imidazole in Buffer A. The protein was dialyzed against Buffer B (25 mM HEPES, 0.1% CHAPS, 10% glycerol, 10 mM BME, pH 8.0) and applied to DEAE ToyoPearl 650M column preequilibrated with the same buffer. The truncated caspase 5 was eluted from the column with 100 mM NaCl in the same buffer. Fractions displaying highest specific activity of truncated caspase 5 using fluorescent peptide substrate, LEED-AMC, were pooled.

EXAMPLE 11

In vitro Activation and Preparation of Polypeptide

Pro-IL-18 prepared and purified as described in Examples 1 and 2 was incubated with truncated caspase 5 at 1:500 w/w ratio for 3 hours at room temperature. The cleavage reaction of prodomain was completed >90% according to SDS-PAGE analysis. To the reaction mixture, 140 ml of NiNTA agarose in Buffer D was added, incubated for one hour, and poured to sintered glass funnel to recover unbound material containing mainly mature IL-18. Small amounts of remaining pro-IL-18, prodomain, truncated caspase 5, and other impurities were bound to NINTA agarose. The unbound solution was adjusted to 25 mM DTT, incubated for one hour to complete reduction reaction, adjusted the pH of the solution to 6.0 by adding 2 M phosphoric acid, and concentrated to 86 ml using YM10 membrane. The concentrated sample was applied to Superdex 75 column equilibrated with 10 mM NaPhosphate pH 6.0 containing 0.1M NaCl. Pooled fractions contained 560 mg of mature IL-18.

EXAMPLE 12

In vivo Activation and Preparation of Polypeptide

Activation of IL-18 can also be achieved in vivo through the simultaneous expression of human precursor IL-18 and truncated caspase 5. Pro-IL-18 was co-expressed bicistronically in *E. coli* from a single transcript with human truncated caspase 5 within the expression plasmid, pET28-ProIL18/Casp5 (FIG. 9). The human pro-IL-18 gene is subcloned into pET28a (Novagen) under the control of the T7 promoter including an efficient Shine-Dalgarno sequence for optimal translation initiation from the Pro-IL-18 sequence (FIG. 10). The truncated caspase 5 gene (Ile146 to Asn418) was subcloned immediately after the Pro-IL-18 sequence including a defective Shine-Dalgarno sequence, permitting minimal translation initiation from the truncated caspase 5 sequence. A T7 terminator sequence was included for translational termination following the bicistronic transcription unit. The resultant construct was then transfected into a B1L21 (DE3) host containing an inducible chromosomal copy of the T7 polymerase gene. Induction of this construct in this host with 1 mM IPTG resulted in the coordinate transcription and translation of pro-IL-18 and pro-caspase 5. Nascently translated pro-caspase 5 is autoprocessed to an active species which initiates the proteolytic activation of pro-IL-18.

EXAMPLE 13

Purification of Human IL-18 Coexpressed With Truncated Caspase 5

66 g of *E. coli* cells expressing IL-18 as described in Example 12 were suspended in 130 ml of 0.1 M HEPES pH 7.5 containing 1 mM EDTA and 10 mM DTT (entire process was performed at 4° C. and in the presence of 10 mM DTT except the last step to maintain free SH) and lysed at 15,000 psi by two passes using Microfluidics. The lysate (230 ml) was centrifuged at 34,000 xg for 30 min. The supernatant (200 ml) was diluted to 1 L with 25 mM HEPES pH 7.0 and flowed through two columns in tandem, ToyoPearl SP 650M and ToyoPearl DEAE 650M. Much of the impurities derived from *E. coli* cells were bound to the columns. The flow-through material was adjusted to pH 9.5 with 25 mM bistris propane, diluted to 2 L and applied to Source 15Q column equilibrated with 25 mM bistris propane HCl pH 9.5. The column was eluted with a linear gradient of 0 to 0.5 M NaCl in the same buffer. Fractions containing IL-18 were identified using Vydac C4 RP-HPLC and pooled (250 ml). The pool was concentrated to 50 ml using YM10 membrane and applied to Superdex 75 column which was preequilibrated with 10 mM NaPO4 pH 6.0 containing 1 mM EDTA and 0.15 M NaCl (no DTT for in vivo use).

EXAMPLE 14

Preparation of Ubiquitin/Pro-IL-18/Ubp1

The 76 amino acid ubiquitin coding sequence is fused in frame with the start of mature human IL-18 through blunt end ligation such that the first tyrosine codon of mature IL-18 immediately follows the glycine 76 codon of ubiquitin. The gene fusion is then subcloned into a pET vector under the control of the T7 promoter including an efficient Shine-Dalgarno sequence for optimal translation initiation from the ubiquitin-IL-18 gene sequence. The full-length Ubp-1 gene is then subcloned immediately following IL-18 including a defective Shine-Dalgarno sequence for minimal translation of Ubp-1. FIG. 18 depicts the sequence of UbIL-18/Ubp-1 expression cassette within pET28. FIG. 19 depicts the annotated sequence of UbIL-18/Ubp-1 within pET28. Numbering corresponds to the position within pET28.

EXAMPLE 15

In vivo Activation and Preparation of IL-18

The construct of Example 14 was then transfected into a BL21 (DE3) host. Induction with 1 mM IPTG resulted in the coordinate transcription and translation of Ubiquitin-IL-18 and Ubp-1. The enzymatic action of Ubp-1 led to the efficient processing of Ub-IL-18 to mature active IL-18 which can then be directly purified from *E. coli* lysates by conventional methods. FIG. 20 illustrates the time course of IL-18 expression and processing at 30° C. and 37° C. following induction with 1 mM IPTG. The top arrow indicates the portion of unprocessed UB-IL-18 in Lane 1. Bottom arrow indicates the portion of processed IL-18 in Lane 3. (Western blot detection using anti-IL-18 antisera.)

EXAMPLE 16

Purification of Human IL-18 Coexpressed with Ubiquitin 66 g of *E. coli* cells expressing IL-18 as described in Example 15 were suspended in 130 ml of 0.1 M HEPES pH 7.5 containing 1 mM EDTA and 10 mM DTT (entire process was performed at 4° C. and in the presence of 10 mM DTT except the last step to maintain free SH) and lysed at 15,000 psi by two passes using Microfluidics. The lysate (230 ml) was centrifuged at 34,000 xg for 30 min. The supernatant (200 ml) was diluted to 1 L with 25 mM HEPES pH 7.0 and flowed through two columns in tandem, ToyoPearl SP 650M and ToyoPearl DEAE 650M. Much of the impurities derived from *E. coli* cells were bound to the columns. The flow-through material was adjusted to pH 9.5 with 25 mM bistris propane, diluted to 2 L and applied to Source 15Q column equilibrated with 25 MM bistris propane HCl pH 9.5. The column was eluted with a linear gradient of 0 to 0.5 M NaCl in the same buffer. Fractions containing IL-18 were identified using Vydac C4 RP-BPLC and pooled (250 ml). The pool was concentrated to 50 ml using YM10 membrane and applied to Superdex 75 column which was preequilibrated with 10 mM NaPO4 pH 6.0 containing 1 mM EDTA and 0.15 M NaCl (no DTT for in vivo use).

While there has been described what is at present considered to be the preferred embodiments of the invention, it will be understood the various modifications may be made therein, and it is intended to cover in the appended claims all such modifications as fall within the true spirit and scope of the invention.

We claim:

1. A method for producing an active human IL-18 polypeptide from a human precursor IL-18 polypeptide, said method comprising the steps of:

(i) co-expressing bicistronically a caspase 5 polypeptide consisting of the amino acid sequence of SEQ ID NO:6, with a human precursor IL-18 polypeptide consisting of the amino acid sequence of SEQ ID NO:1; and (ii) purifying the active human IL-18 polypeptide (SEQ ID NO:3).

* * * * *

SEQUENCE LISTING

```
<160> NUMBER OF SEQ ID NOS: 12

<210> SEQ ID NO 1
<211> LENGTH: 193
<212> TYPE: PRT
<213> ORGANISM: Homo sapien

<400> SEQUENCE: 1

Met Ala Ala Glu Pro Val Glu Asp Asn Cys Ile Asn Phe Val Ala Met
 1               5                  10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
    130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp


<210> SEQ ID NO 2
<211> LENGTH: 582
<212> TYPE: DNA
<213> ORGANISM: Homo sapien

<400> SEQUENCE: 2

atggctgctg aaccagtaga agacaattgc atcaactttg tggcaatgaa atttattgac      60

aatacgcttt actttatagc tgaagatgat gaaaacctgg aatcagatta ctttggcaag     120

cttgagagca aactatcggt cattcgtaat ttaaatgacc aggtcctatt tatcgaccaa     180

gggaatcgtc cactattcga ggacatgaca gacagtgact gccgagacaa tgcgccgcga     240

accattttca ttatatctat gtacaaggat tctcagccgc gcggaatggc cgtaactatt     300

tctgtcaaat gtgaaaagat atccacgctg tcgtgtgaga acaagattat tagtttcaaa     360
```

-continued

```
gagatgaatc cgccggataa tatcaaggac acgaagtctg atatcatatt tttccagcgc    420

agcgtgccgg ggcacgataa caagatgcaa tttgaatcat ccagctatga agggtacttt    480

cttgcatgcg agaaggaacg cgatctcttt aaacttattt taaagaaaga ggacgagcta    540

ggcgatcgca gcattatgtt cactgtccaa aatgaagact ag                       582
```

```
<210> SEQ ID NO 3
<211> LENGTH: 157
<212> TYPE: PRT
<213> ORGANISM: Homo sapien

<400> SEQUENCE: 3

Tyr Phe Gly Lys Leu Glu Ser Lys Leu Ser Val Ile Arg Asn Leu Asn
 1               5                  10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

```
<210> SEQ ID NO 4
<211> LENGTH: 282
<212> TYPE: PRT
<213> ORGANISM: Homo sapien

<400> SEQUENCE: 4

Met Gly His His His His His His Gly Ala Leu Lys Leu Cys Pro His
 1               5                  10                  15

Glu Glu Phe Leu Arg Leu Cys Lys Glu Arg Ala Glu Glu Ile Tyr Pro
            20                  25                  30

Ile Lys Glu Arg Asn Asn Arg Thr Arg Leu Ala Leu Ile Ile Cys Asn
        35                  40                  45

Thr Glu Phe Asp His Leu Pro Pro Arg Asn Gly Ala Asp Phe Asp Ile
    50                  55                  60

Thr Gly Met Lys Glu Leu Leu Glu Gly Leu Asp Tyr Ser Val Asp Val
65                  70                  75                  80

Glu Glu Asn Leu Thr Ala Arg Asp Met Glu Ser Ala Leu Arg Ala Phe
                85                  90                  95

Ala Thr Arg Pro Glu His Lys Ser Ser Asp Ser Thr Phe Leu Val Leu
            100                 105                 110

Met Ser His Gly Ile Leu Glu Gly Ile Cys Gly Thr Val His Asp Glu
        115                 120                 125

Lys Lys Pro Asp Val Leu Leu Tyr Asp Thr Ile Phe Gln Ile Phe Asn
```

-continued

```
    130                 135                 140

Asn Arg Asn Cys Leu Ser Leu Lys Asp Lys Pro Lys Val Ile Ile Val
145                 150                 155                 160

Gln Ala Cys Arg Gly Ala Asn Arg Gly Glu Leu Trp Val Arg Asp Ser
                165                 170                 175

Pro Thr Ser Leu Glu Val Ala Ser Ser Gln Ser Ser Glu Asn Leu Glu
            180                 185                 190

Glu Asp Ala Val Tyr Lys Thr His Val Glu Lys Asp Phe Ile Ala Phe
        195                 200                 205

Cys Ser Ser Thr Pro His Asn Val Ser Trp Arg Asp Ser Thr Met Gly
    210                 215                 220

Ser Ile Phe Ile Thr Gln Leu Ile Thr Cys Phe Gln Lys Tyr Ser Trp
225                 230                 235                 240

Cys Cys His Leu Glu Glu Val Phe Arg Lys Val Gln Gln Ser Phe Glu
                245                 250                 255

Thr Pro Arg Ala Lys Ala Gln Met Pro Thr Ile Glu Arg Leu Ser Met
            260                 265                 270

Thr Arg Tyr Phe Tyr Leu Phe Pro Gly Asn
        275                 280
```

<210> SEQ ID NO 5
<211> LENGTH: 849
<212> TYPE: DNA
<213> ORGANISM: Homo sapien

<400> SEQUENCE: 5

```
atgggccatc atcatcatca tcatggcgcc ctcaagcttt gtcctcatga agaattcctg     60

agactatgta aagaaagagc tgaagagatc tatccaataa aggagagaaa caaccgcaca    120

cgcctggctc tcatcatatg caatacagag tttgaccatc tgcctccgag gaatggagct    180

gactttgaca tcacagggat gaaggagcta cttgagggtc tggactatag tgtagatgta    240

gaagagaatc tgacagccag ggatatggag tcagcgctga gggcatttgc taccagacca    300

gagcacaagt cctctgacag cacattcttg gtactcatgt ctcatggcat cctggaggga    360

atctgcggaa ctgtgcatga tgagaaaaaa ccagatgtgc tgctttatga caccatcttc    420

cagatattca acaaccgcaa ctgcctcagt ctgaaggaca aacccaaggt catcattgtc    480

caggcctgca gaggtgcaaa ccgtggggaa ctgtgggtca gagactctcc agcatccttg    540

gaagtggcct cttcacagtc atctgagaac ctggaggaag atgctgttta caagacccac    600

gtggagaagg acttcattgc tttctgctct tcaacgccac acaacgtgtc ctggagagac    660

agcacaatgg gctctatctt catcacacaa ctcatcacat gcttccagaa atattcttgg    720

tgctgccacc tagaggaagt atttcggaag gtacagcaat catttgaaac tccaagggcc    780

aaagctcaaa tgcccaccat agaacgactg tccatgacaa gatatttcta cctctttcct    840

ggcaattga                                                            849
```

<210> SEQ ID NO 6
<211> LENGTH: 282
<212> TYPE: PRT
<213> ORGANISM: Homo sapien

<400> SEQUENCE: 6

```
Met Gly His His His His His His Gly Ile Leu Lys Leu Cys Pro Arg
 1               5                  10                  15

Glu Glu Phe Leu Arg Leu Cys Lys Lys Asn His Asp Glu Ile Tyr Pro
```

-continued

```
            20                  25                  30

Ile Lys Lys Arg Glu Asp Arg Arg Arg Leu Ala Leu Ile Ile Cys Asn
        35                  40                  45

Thr Lys Phe Asp His Leu Pro Ala Arg Asn Gly Ala His Tyr Asp Ile
    50                  55                  60

Val Gly Met Lys Arg Leu Leu Gln Gly Leu Gly Tyr Thr Val Val Asp
65                  70                  75                  80

Glu Lys Asn Leu Thr Ala Arg Asp Met Glu Ser Val Leu Arg Ala Phe
                85                  90                  95

Ala Ala Arg Pro Glu His Lys Ser Ser Asp Ser Thr Phe Leu Val Leu
            100                 105                 110

Met Ser His Gly Ile Leu Glu Gly Ile Cys Gly Thr Ala His Lys Lys
        115                 120                 125

Lys Lys Pro Asp Val Leu Leu Tyr Asp Thr Ile Phe Gln Ile Phe Asn
    130                 135                 140

Asn Arg Asn Cys Leu Ser Leu Lys Asp Lys Pro Lys Val Ile Ile Val
145                 150                 155                 160

Gln Ala Cys Arg Gly Glu Lys His Gly Glu Leu Trp Val Arg Asp Ser
                165                 170                 175

Pro Ala Ser Leu Ala Val Ile Ser Ser Gln Ser Ser Glu Asn Leu Glu
            180                 185                 190

Ala Asp Ser Val Cys Lys Ile His Glu Glu Lys Asp Phe Ile Ala Phe
        195                 200                 205

Cys Ser Ser Thr Pro His Asn Val Ser Trp Arg Asp Arg Thr Arg Gly
    210                 215                 220

Ser Ile Phe Ile Thr Glu Leu Ile Thr Cys Phe Gln Lys Tyr Ser Cys
225                 230                 235                 240

Cys Cys His Leu Met Glu Ile Phe Arg Lys Val Gln Lys Ser Phe Glu
                245                 250                 255

Val Pro Gln Ala Lys Ala Gln Met Pro Thr Ile Glu Arg Ala Thr Leu
            260                 265                 270

Thr Arg Asp Phe Tyr Leu Phe Pro Gly Asn
        275                 280
```

<210> SEQ ID NO 7
<211> LENGTH: 849
<212> TYPE: DNA
<213> ORGANISM: Homo sapien

<400> SEQUENCE: 7

```
atgggccatc atcatcatca tcatggcata ctcaaacttt gtcctcgtga agaattcctg      60

agactgtgta aaaaaaatca tgatgagatc tatccaataa aaaagagaga ggaccgcaga     120

cgcctggctc tcatcatatg caatacaaag tttgatcacc tgcctgcaag gaatggggct     180

cactatgaca tcgtggggat gaaaaggctg cttcaaggcc tgggctacac tgtggttgac     240

gaaaagaatc tcacagccag ggatatggag tcagtgctga gggcatttgc tgccagacca     300

gagcacaagt cctctgacag cacgttcttg gtactcatgt ctcatggcat cctagaggga     360

atctgcggaa ctgcgcataa aaagaaaaaa ccggatgtgc tgctttatga caccatcttc     420

cagatattca acaaccgcaa ctgcctcagt ctaaaggaca aacccaaggt catcattgtc     480

caggcctgca gaggtgaaaa acatggggaa ctctgggtca gagactctcc agcatccttg     540

gcagtcatct cttcacagtc atctgagaac ctggaggcag attctgtttg caagatccac     600

gaggagaagg acttcattgc tttctgttct tcaacaccac ataacgtgtc ctggagagac     660
```

-continued

```
cgcacaaggg gctccatctt cattacggaa ctcatcacat gcttccagaa atattcttgc    720

tgctgccacc taatggaaat atttcggaag gtacagaaat catttgaagt tccacaggct    780

aaagcccaga tgcccaccat agaacgagca accttgacaa gagatttcta cctctttcct    840

ggcaattga                                                            849
```

<210> SEQ ID NO 8
<211> LENGTH: 1743
<212> TYPE: DNA
<213> ORGANISM: Homo sapien

<400> SEQUENCE: 8

```
agatctcgat cccgcgaaat taatacgact cactataggg gaattgtgag cggataacaa     60

ttcccctcta gaccacacct taaggaggat ataacatatg gctgctgaac cagtagaaga    120

caattgcatc aactttgtgg caatgaaatt tattgacaat acgctttact ttatagctga    180

agatgatgaa aacctggaat cagattactt tggcaagctt gagagcaaac tatcggtcat    240

tcgtaattta aatgaccagg tcctatttat cgaccaaggg aatcgtccac tattcgagga    300

catgacagac agtgactgcc gagacaatgc gccgcgaacc attttcatta tatctatgta    360

caaggattct cagccgcgcg gaatggccgt aactatttct gtcaaatgtg aaaagatatc    420

cacgctgtcg tgtgagaaca agattattag tttcaaagag atgaatccgc cggataatat    480

caaggacacg aagtctgata tcatattttt ccagcgcagc gtgccggggc acgataacaa    540

gatgcaattt gaatcatcca gctatgaagg gtactttctt gcatgcgaga aggaacgcga    600

tctctttaaa cttattttaa agaaagagga cgagctaggc gatcgcagca ttatgttcac    660

tgtccaaaat gaagactagt ggaggatata ataccaggaa taaataaaat ccatgggcca    720

tcatcatcat catcatggcg ccctcaagct ttgtcctcat gaagaattcc tgagactatg    780

taaagaaaga gctgaagaga tctatccaat aaaggagaga aacaaccgca cacgcctggc    840

tctcatcata tgcaatacag agtttgacca tctgcctccg aggaatggag ctgactttga    900

catcacaggg atgaaggagc tacttgaggg tctggactat agtgtagatg tagaagagaa    960

tctgacagcc agggatatgg agtcagcgct gagggcattt gctaccagac cagagcacaa   1020

gtcctctgac agcacattct tggtactcat gtctcatggc atcctggagg gaatctgcgg   1080

aactgtgcat gatgagaaaa aaccagatgt gctgctttat gacaccatct tccagatatt   1140

caacaaccgc aactgcctca gtctgaagga caaacccaag gtcatcattg tccaggcctg   1200

cagaggtgca aaccgtgggg aactgtgggt cagagactct ccagcatcct tggaagtggc   1260

ctcttcacag tcatctgaga acctggagga agatgctgtt tacaagaccc acgtggagaa   1320

ggacttcatt gctttctgct cttcaacgcc acacaacgtg tcctggagag acagcacaat   1380

gggctctatc ttcatcacac aactcatcac atgcttccag aaatattctt ggtgctgcca   1440

cctagaggaa gtatttcgga aggtacagca atcatttgaa actccaaggg ccaaagctca   1500

aatgcccacc atagaacgac tgtccatgac aagatatttc tacctctttc ctggcaattg   1560

aaaatggatc cgaattcgag ctccgtcgac aagcttgcgg ccgcactcga gcaccaccac   1620

caccaccact gagatccggc tgctaacaaa gcccgaaagg aagctgagtt ggctgctgcc   1680

accgctgagc aataactagc ataacccctt ggggcctcta aacgggtctt gaggggtttt   1740

ttg                                                                 1743
```

<210> SEQ ID NO 9

-continued

<211> LENGTH: 1464
<212> TYPE: DNA
<213> ORGANISM: Homo sapien

<400> SEQUENCE: 9
atggctgctg aaccagtaga agacaattgc atcaactttg tggcaatgaa atttattgac 60
aatacgcttt actttatagc tgaagatgat gaaaacctgg aatcagatta ctttggcaag 120
cttgagagca aactatcggt cattcgtaat ttaaatgacc aggtcctatt tatcgaccaa 180
gggaatcgtc cactattcga ggacatgaca gacagtgact gccgagacaa tgcgccgcga 240
accattttca ttatatctat gtacaaggat tctcagccgc gcggaatggc cgtaactatt 300
tctgtcaaat gtgaaaagat atccacgctg tcgtgtgaga acaagattat tagtttcaaa 360
gagatgaatc cgccggataa tatcaaggac acgaagtctg atatcatatt tttccagcgc 420
agcgtgccgg ggcacgataa caagatgcaa tttgaatcat ccagctatga agggtacttt 480
cttgcatgcg agaaggaacg cgatctcttt aaacttattt taaagaaaga ggacgagcta 540
ggcgatcgca gcattatgtt cactgtccaa aatgaagact agtggaggat ataataccag 600
gaataaataa aatccatggg ccatcatcat catcatcatg gcatactcaa actttgtcct 660
cgtgaagaat tcctgagact gtgtaaaaaa aatcatgatg agatctatcc aataaaaaag 720
agagaggacc gcagacgcct ggctctcatc atatgcaata caaagtttga tcacctgcct 780
gcaaggaatg gggctcacta tgacatcgtg gggatgaaaa ggctgcttca aggcctgggc 840
tacactgtgg ttgacgaaaa gaatctcaca gccagggata tggagtcagt gctgagggca 900
tttgctgcca gaccagagca caagtcctct gacagcacgt tcttggtact catgtctcat 960
ggcatcctag agggaatctg cggaactgcg cataaaaaga aaaaaccgga tgtgctgctt 1020
tatgacacca tcttccagat attcaacaac cgcaactgcc tcagtctaaa ggacaaaccc 1080
aaggtcatca ttgtccaggc ctgcagaggt gaaaaacatg gggaactctg ggtcagagac 1140
tctccagcat ccttggcagt catctcttca cagtcatctg agaacctgga ggcagattct 1200
gtttgcaaga tccacgagga gaaggacttc attgctttct gttcttcaac accacataac 1260
gtgtcctgga gagaccgcac aaggggctcc atcttcatta cggaactcat cacatgcttc 1320
cagaaatatt cttgctgctg ccacctaatg gaaatatttc ggaaggtaca gaaatcattt 1380
gaagttccac aggctaaagc ccagatgccc accatagaac gagcaacctt gacaagagat 1440
ttctacctct ttcctggcaa ttga 1464

<210> SEQ ID NO 10
<211> LENGTH: 233
<212> TYPE: PRT
<213> ORGANISM: Homo sapien

<400> SEQUENCE: 10

```
Met Gln Ile Phe Val Lys Thr Leu Thr Gly Lys Thr Ile Thr Leu Glu
 1               5                  10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Tyr Phe Gly Lys
65                  70                  75                  80
```

-continued

```
Leu Glu Ser Lys Leu Ser Val Ile Arg Asn Leu Asn Asp Gln Val Leu
                85                  90                  95

Phe Ile Asp Gln Gly Asn Arg Pro Leu Phe Glu Asp Met Thr Asp Ser
            100                 105                 110

Asp Cys Arg Asp Asn Ala Pro Arg Thr Ile Phe Ile Ile Ser Met Tyr
        115                 120                 125

Lys Asp Ser Gln Pro Arg Gly Met Ala Val Thr Ile Ser Val Lys Cys
    130                 135                 140

Glu Lys Ile Ser Thr Leu Ser Cys Glu Asn Lys Ile Ile Ser Phe Lys
145                 150                 155                 160

Glu Met Asn Pro Pro Asp Asn Ile Lys Asp Thr Lys Ser Asp Ile Ile
                165                 170                 175

Phe Phe Gln Arg Ser Val Pro Gly His Asp Asn Lys Met Gln Phe Glu
            180                 185                 190

Ser Ser Ser Tyr Glu Gly Tyr Phe Leu Ala Cys Glu Lys Glu Arg Asp
        195                 200                 205

Leu Phe Lys Leu Ile Leu Lys Lys Glu Asp Glu Leu Gly Asp Arg Ser
    210                 215                 220

Ile Met Phe Thr Val Gln Asn Glu Asp
225                 230
```

<210> SEQ ID NO 11
<211> LENGTH: 702
<212> TYPE: DNA
<213> ORGANISM: Homo sapien

<400> SEQUENCE: 11

```
atgcagatct tcgtcaagac gttaaccggt aaaaccataa ctctagaagt tgaatcttcc     60

gataccatcg acaacgttaa gtcgaaaatt caagacaagg aaggcattcc acctgatcaa    120

caaagattga tctttgccgg taagcagctc gaagacggta gaacgctgtc tgattacaac    180

attcagaagg agtcgacctt acatcttgtc ttaagactaa gaggagggta ctttggcaag    240

cttgagagca aactatcggt cattcgtaat ttaaatgacc aggtcctatt tatcgaccaa    300

gggaatcgtc cactattcga ggacatgaca gacagtgact gccgagacaa tgcgccgcga    360

accattttca ttatatctat gtacaaggat tctcagccgc gcggaatggc cgtaactatt    420

tctgtcaaat gtgaaaagat atccacgctg tcgtgtgaga acaagattat tagtttcaaa    480

gagatgaatc cgccggataa tatcaaggac acgaagtctg atatcatatt tttccagcgc    540

agcgtgccgg ggcacgataa caagatgcaa tttgaatcat ccagctatga agggtacttt    600

cttgcatgcg agaaggaacg cgatctcttt aaacttattt taaagaaaga ggacgagcta    660

ggcgatcgca gcattatgtt cactgtccaa aatgaagact ag                       702
```

<210> SEQ ID NO 12
<211> LENGTH: 3419
<212> TYPE: DNA
<213> ORGANISM: Homo sapien

<400> SEQUENCE: 12

```
agatctcgat cccgcgaaat taatacgact cactataggg gaattgtgag cggataacaa     60

ttcccctcta gaccacacct taaggaggat ataacatatg cagatcttcg tcaagacgtt    120

aaccggtaaa accataactc tagaagttga atcttccgat accatcgaca acgttaagtc    180

gaaaattcaa gacaaggaag gcattccacc tgatcaacaa agattgatct ttgccggtaa    240

gcagctcgag gacggtagaa cgctgtctga ttacaacatt cagaaggagt cgaccttaca    300
```

-continued

```
tcttgtctta agactaagag gagggtactt tggcaagctt gagagcaaac tatcggtcat    360
tcgtaattta aatgaccagg tcctatttat cgaccaaggg aatcgtccac tattcgagga    420
catgacagac agtgactgcc gagacaatgc gccgcgaacc attttcatta tatctatgta    480
caaggattct cagccgcgcg gaatggccgt aactatttct gtcaaatgtg aaaagatatc    540
cacgctgtcg tgtgagaaca agattattag tttcaaagag atgaatccgc cggataatat    600
caaggacacg aagtctgata tcatattttt ccagcgcagc gtgccggggc acgataacaa    660
gatgcaattt gaatcatcca gctatgaagg gtactttctt gcatgcgaga aggaacgcga    720
tctctttaaa cttattttaa agaaagagga cgagctaggc gatcgcagca ttatgttcac    780
tgtccaaaat gaagactagt ggaggatata ataccaggaa taaataaaat ccatgggcca    840
tcatcatcat catcatggca tggatgaaag caagataaac agtttattac aatttttatt    900
tggttcccga caggattttt tgagaaattt taaaacttgg agtaacaaca ataacaatct    960
atcgatttat ttattaattt ttggcatagt agtatttttt tataaaaaac cagaccatct   1020
aaactacatt gttgagagcg ttagtgaaat gacaacaaac ttcagaaata ataatagcct   1080
tagccgttgg ttgcccagaa gtaagtttac ccacttagac gaagagatct tgaaaagagg   1140
tggtttcatt gctggtttag ttaatgatgg taacacttgt tttatgaact ctgttttgca   1200
atcattggca tcatccagag aattaatgga gttcttggac aataatgtca taaggaccta   1260
tgaggagata gaacaaaatg aacacaatga agaaggaaac gggcaagaat ctgctcaaga   1320
tgaagccact cataagaaaa acactcgtaa gggtggcaaa gtttatggta agcataagaa   1380
gaaattgaat aggaagtcaa gttcgaaaga agacgaagaa aagagccagg agccagatat   1440
cactttcagt gtcgccttaa gggatctact ttctgcctta aatgcgaagt attatcggga   1500
taaaccctat ttcaaaacca atagtttatt gaaagcaatg tccaaatctc caagaaaaaa   1560
tattcttctt ggctacgacc aagaggacgc gcaagaattc ttccagaaca tactagccga   1620
gttggaaagt aacgttaaat cattgaatac tgaaaaacta gataccactc cagttgcgaa   1680
atcagaatta cccgatgatg ctttagtagg tcaacttaac cttggtgaag ttggcactgt   1740
ttacattcca actgaacaga ttgatcctaa ctctatacta catgacaagt ccattcaaaa   1800
tttcacacct ttcaaactaa tgactccttt agatggtatc acggcagaaa gaattggttg   1860
tttacagtgt ggtgagaacg gtggcataag atattccgta ttttcgggat taagcttaaa   1920
tttaccgaac gagaatattg gttccacttt aaaattatct cagttattga gcgactggag   1980
taaacctgaa atcatcgaag tcgtagaatg taaccgttgt gccctcacag cagcgcactc   2040
tcatttattt ggtcagttga aagaatttga aaaaaaacct gagggttcga tcccagaaaa   2100
gccaattaac gctgtaaaag atagggtcca tcaaatcgaa gaagttcttg ccaaaccagt   2160
tattgacgat gaagattata agaagttgca tacagcaaat atggtacgta aatgctctaa   2220
atctaagcag attttaatat caagacctcc accattatta tccattcata tcaacagatc   2280
cgtatttgat ccaagaacgt acatgattag aaaaaataac tcgaaagtat tgtttaagtc   2340
aacgttgaat cttgcccctt ggtgttgtga tattaatgaa atcaatttgg atgctcgttt   2400
gccaatgtca aaaaaggaaa aagctgcgca acaagattca agtgaagatg aaaacattgg   2460
cggtgaatac tatacgaaat tacatgaacg cttcgagcag gaatttgaag acagcgagga   2520
agaaaaagaa tacgatgacg cagaggggaa ctatgcgtct cattacaatc ataccaagga   2580
tatcagtaac tatgatcccc taaacggtga agtcgatggc gtgacatccg atgatgaaga   2640
```

-continued

```
tgagtacatt gaagaaaccg atgctttagg gaatacaatc aaaaaaagga tcatagaaca   2700

ttctgatgtt gaaaacgaga atgtaaaaga taatgaagaa ctgcaagaaa tcgacaatgt   2760

gagccttgac gaaccaaaga tcaatgttga agatcaacta gaaacatcat ctgatgagga   2820

agatgttata ccagctccac ctatcaatta tgctaggtca ttttccacag ttccagccac   2880

tccattgaca tattcattgc gctctgtcat tgttcactac ggtacccata attatggtca   2940

ttacattgca tttagaaaat acaggggttg ttggtggaga atatctgatg agactgtgta   3000

cgttgtggac gaagctgaag tcctttcaac acccggtgta tttatgttat tttacgaata   3060

tgactttgat gaagaaactg ggaagatgaa ggatgatttg gaagctattc agagtaataa   3120

tgaagaagat gatgaaaaag agcaggagca aaaaggagtc caggagccaa aggaaagcca   3180

agagcaagga gaaggtgaag agcaagagga aggtcaagag cagatgaagt tcgagagaac   3240

agaagaccat agagatattt ctggtaaaga tgtaaactaa gctcgagcac caccaccacc   3300

accactgaga tccggctgct aacaaagccc gaaaggaagc tgagttggct gctgccaccg   3360

ctgagcaata actagcataa ccccttgggg cctctaaacg ggtcttgagg ggttttttg    3419
```